(12) United States Patent
Nishikawa et al.

(10) Patent No.: US 10,286,222 B2
(45) Date of Patent: May 14, 2019

(54) MAGNETIC STIMULATOR

(75) Inventors: Atsushi Nishikawa, Suita (JP); Youichi Saitoh, Suita (JP); Taishi Fukushima, Suita (JP); Masaki Sekino, Kashiwa (JP); Kuniyoshi Uchida, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 690 days.

(21) Appl. No.: 13/378,333

(22) PCT Filed: Jun. 11, 2010

(86) PCT No.: PCT/JP2010/059969
§ 371 (c)(1),
(2), (4) Date: Mar. 6, 2012

(87) PCT Pub. No.: WO2010/147064
PCT Pub. Date: Dec. 23, 2010

(65) Prior Publication Data
US 2012/0157752 A1    Jun. 21, 2012

(30) Foreign Application Priority Data
Jun. 15, 2009    (JP) .................................. 2009-142461

(51) Int. Cl.
*A61N 2/00*    (2006.01)
*A61N 2/02*    (2006.01)
(Continued)

(52) U.S. Cl.
CPC .................. *A61N 2/02* (2013.01); *A61B 5/05* (2013.01); *A61B 5/6803* (2013.01); *A61N 2/006* (2013.01); *A61N 2/008* (2013.01); *A61B 90/14* (2016.02)

(58) Field of Classification Search
CPC .......... A61N 2/00; A61N 2/002; A61N 2/004; A61N 2/006; A61N 2/008; A61N 2/02
(Continued)

(56) References Cited

U.S. PATENT DOCUMENTS 3,116,365 A    12/1963    Prescott
2003/0073899 A1    4/2003    Ruohonen et al.
(Continued)

FOREIGN PATENT DOCUMENTS

DE    10242542 A1    4/2004
DE    102008034237 A1    2/2010
(Continued)

OTHER PUBLICATIONS

Translation of the International Preliminary Report on Patentability and Written Opinion dated Jan. 26, 2012 in International Patent Application No. PCT/JP2010/059969.
(Continued)

*Primary Examiner* — Carrier R Dorna
(74) *Attorney, Agent, or Firm* — Sughrue Mion, PLLC

(57) ABSTRACT

Provided is a magnetic stimulator for applying magnetic stimulation to a particular portion of a subject. This magnetic stimulator includes: a magnetic field generating means including at least a stimulation coil configured to generate a dynamic magnetic field so as to apply the magnetic stimulation; a coil holder operated to displace a relative position of the magnetic field generating means with respect to the particular portion of the subject; a plurality of magnetic field sensors each configured to detect the magnetic field generated by the magnetic field generating means; and a user interface section configured to provide instruction information based on a result of the detection of the magnetic field generated by the magnetic field generating means, the instruction information indicating an operation of displacement to be performed using the coil holder, the detection being made by the magnetic field sensors either before or during the magnetic stimulation.

35 Claims, 24 Drawing Sheets

(51) Int. Cl.
*A61B 5/05* (2006.01)
*A61B 5/00* (2006.01)
*A61B 90/14* (2016.01)

(58) Field of Classification Search
USPC ........................................................ 600/9–15
See application file for complete search history.

(56) References Cited

U.S. PATENT DOCUMENTS

| | | |
|---|---|---|
| 2004/0039279 A1 | 2/2004 | Ruohonen |
| 2005/0025353 A1 | 2/2005 | Kaneko et al. |
| 2005/0148808 A1 | 7/2005 | Cameron et al. |
| 2005/0193451 A1 | 9/2005 | Quistgaard et al. |
| 2005/0234286 A1 | 10/2005 | Riehl et al. |
| 2006/0122496 A1 | 6/2006 | George et al. |
| 2006/0161039 A1 | 7/2006 | Juliana et al. |
| 2006/0287566 A1 | 12/2006 | Zangen et al. |
| 2007/0078466 A1 | 4/2007 | Bodduluri et al. |
| 2008/0139871 A1 | 6/2008 | Muntermann |
| 2008/0161716 A1 | 7/2008 | Livne et al. |
| 2009/0187062 A1 | 7/2009 | Saitoh |
| 2009/0216067 A1 | 8/2009 | Lebosse et al. |
| 2009/0227830 A1 | 9/2009 | Pillutla et al. |
| 2010/0036191 A1 | 2/2010 | Walter et al. |
| 2010/0234871 A1 | 9/2010 | Qureshi et al. |
| 2011/0230701 A1 | 9/2011 | Simon et al. |
| 2014/0179981 A1 | 6/2014 | Katz et al. |

FOREIGN PATENT DOCUMENTS

| | | |
|---|---|---|
| EP | 2 008 687 A1 | 12/2008 |
| EP | 2 444 119 A1 | 4/2012 |
| JP | H10-49218 A | 2/1998 |
| JP | 11-197259 A | 7/1999 |
| JP | 2003-180649 A | 7/2003 |
| JP | 2004-636 A | 1/2004 |
| JP | 2006-102406 A | 4/2006 |
| JP | 2006-320425 A | 11/2006 |
| JP | 2007-520290 A | 7/2007 |
| JP | 2008-505662 A | 2/2008 |
| JP | 2008-528108 A | 7/2008 |
| JP | 2008-532722 A | 8/2008 |
| JP | 2009-509671 A | 3/2009 |
| JP | 2011-104385 A | 6/2011 |
| WO | 03/098268 A1 | 11/2003 |
| WO | WO 2005/075019 A1 | 8/2005 |
| WO | WO 2005/102187 A2 | 11/2005 |
| WO | WO 2006/100677 A2 | 9/2006 |
| WO | 2007/041267 A2 | 4/2007 |
| WO | WO 2007/123147 A1 | 11/2007 |
| WO | 2009/063435 A1 | 5/2009 |
| WO | 2012/059917 A1 | 5/2012 |

OTHER PUBLICATIONS

International Search Report dated Dec. 4, 2012 issued in PCT/JP2012/077523.
International Search Report dated Dec. 4, 2012 issued in PCT/JP2012/077524.
European Search Report dated Apr. 8, 2015 issued in application No. 12843321.6-1659.
European Search Report dated Apr. 8, 2015 issued in application No. 12844573.1-1659.
Office Action dated Feb. 29, 2016 from the United States Patent and Trademark Office issued in corresponding U.S. Appl. No. 14/353,688.
Lebosse et al., "A Robotic System for Automated Image-Guided Transcranial Magnetic Stimulation", 2007 IEEE/NIH Life Science Systems and Applications Workshop (2007): 55-58. Web. Feb. 18, 2016, 4 pages total.
Office Action dated Feb. 26, 2016 from the United States Patent and Trademark Office issued in corresponding U.S. Appl. No. 14/353,559.
Communication dated Oct. 11, 2016, from the United States Patent and Trademark Office in counterpart U.S. Appl. No. 14/353,559.
An Office Action dated Jul. 13, 2017, which issued during the prosecution of U.S. Appl. No. 14/353,559.
Communication dated Nov. 8, 2018, from European Patent Office in counterpart application No. 12843321.6.

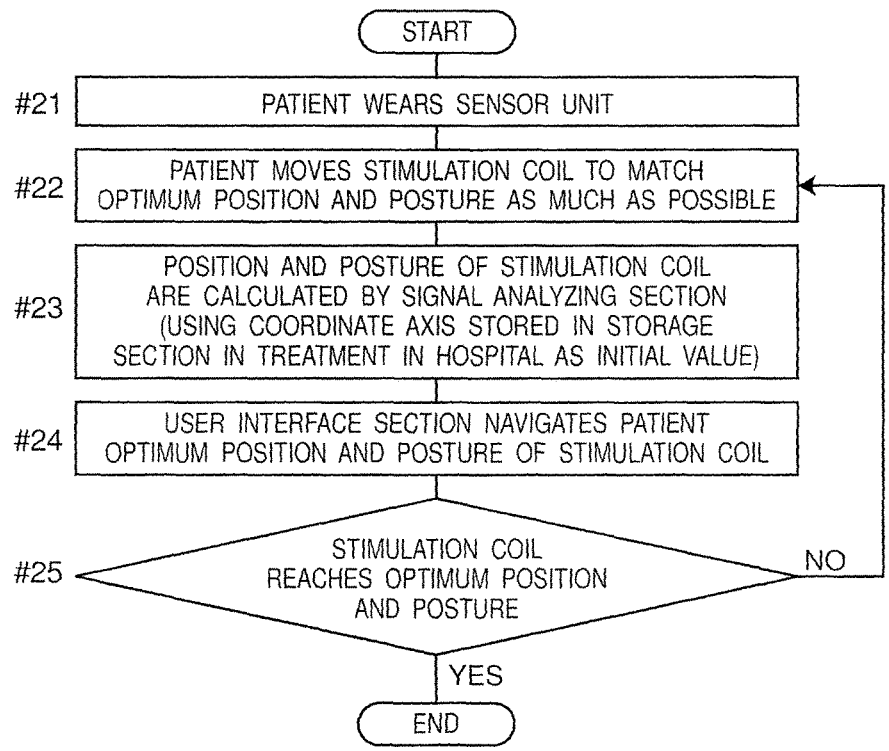
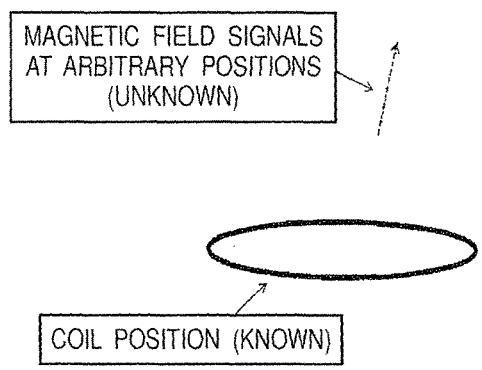

RATIO IN WHICH ERROR FROM TRUE VALUE IS WITHIN 10 (cm)

RATIO IN WHICH ERROR FROM TRUE VALUE IS WITHIN 5 (cm)

CORRELATION CHART 1 BETWEEN FUNCTION f AND POSITION ERROR

CORRELATION CHART 2 BETWEEN FUNCTION f AND POSITION ERROR

CORRELATION CHART 1 BETWEEN FUNCTION f AND ROLL ANGLE ERROR

CORRELATION CHART 2 BETWEEN FUNCTION f AND ROLL ANGLE ERROR

CORRELATION CHART 1 BETWEEN FUNCTION f AND PITCH ANGLE ERROR

CORRELATION CHART 2 BETWEEN FUNCTION f AND PITCH ANGLE ERROR

CORRELATION CHART 1 BETWEEN FUNCTION f AND YAW ANGLE ERROR

CORRELATION CHART 2 BETWEEN FUNCTION f AND YAW ANGLE ERROR

CORRELATION CHART BETWEEN $f_0$
AND AVAILABILITY OF COIL POSITION DETERMINATION

CONVERGENCE RATE DEPENDING ON RELIABILITY OF T10, T30, AND T50

CONVERGENCE RATE DEPENDING ON RELIABILITY OF T11, T31, AND T51

CONVERGENCE RATE DEPENDING ON RELIABILITY OF T12, T32, AND T52

CONVERGENCE RATE DEPENDING ON RELIABILITY OF T13, T33, AND T53

MAGNETIC STIMULATOR

CROSS REFERENCE TO RELATED APPLICATIONS

This application is a National Stage of International Application No. PCT/JP2010/059969 filed Jun. 11, 2010, claiming priority based on Japanese Patent Application No. 2009-142461, filed Jun. 15, 2009, the contents of all of which are incorporated herein by reference in their entirety.

TECHNICAL FIELD

The present invention relates to a magnetic stimulator for applying magnetic stimulation to a particular portion of a subject (such as a patient or an examinee, for example).

BACKGROUND ART

In recent years, a transcranial magnetic stimulation treatment is increasingly receiving attentions as a treatment method to various patients of neural diseases for which medication is not always effective. The transcranial magnetic stimulation treatment is a relatively new treatment method for applying magnetic stimulation to a particular portion of the brain (brain nerve, for example) by a magnetic field generating source provided on the surface of a patient s scalp, thereby capable of providing a treatment and/or relieving symptoms. Unlike the conventional electric stimulation requiring a craniotomy procedure and using an implanted electrode that makes a patient highly uncomfortable, the transcranial magnetic stimulation treatment is expected to be broadly used as a treatment method that is non-invasive and less stressful for patients.

As a specific method of such a transcranial magnetic stimulation treatment, there is known a method of applying electrical current to a coil provided on the surface of a patient s scalp, regionally generating a small pulsed magnetic field, generating eddy current within a cranium based on a principle of electromagnetic induction, and applying stimulation to the brain nerve immediately under the coil (see Patent Literature 1, for example).

According to Patent Literature 1, it is confirmed that the transcranial magnetic stimulation treatment provided according to the above method effectively relieves intractable neuropathic pains, and in addition, provides a higher effect for pain relief by applying focal stimulation more accurately. However, it is also disclosed that optimum stimulating regions of individual patients are delicately different.

Therefore, in order to achieve a higher effect with the transcranial magnetic stimulation treatment, it is important how an optimum stimulating region on a patient s head is determined for each patient, or more specifically, how three-dimensional positioning of a stimulation coil to the patient s head is performed accurately. It should be noted that it is also known that even if the position of the stimulation coil is the same, an achieved effect varies depending on an orientation (posture) of the coil.

Known configurations of the positioning of such a stimulation coil include positioning of a stimulation coil on the patient s head utilizing an optical tracking system using infrared rays (see Patent Literatures 2 and 3, for example), and some are commercially available and applied in clinical settings. In addition, Patent Literature 4 discloses a device capable of positioning a stimulation coil on the patient s head using an articulated robot.

Further, Patent Literature 1 also discloses that a pain relief effect by performing the transcranial magnetic stimulation treatment described above lasts for on the order of several hours, but not for days or longer. Therefore, in terms of the pain relief, it is considered to be desirable to perform the treatment continuously, without taking a long interval, preferably every day. In order to allow such a continuous treatment to be performed without imposing too much burden on a patient such as physically and in terms of time, it is ideal that a treatment at home or at a personal doctor s office in the neighborhood be made possible.

PATENT LITERATURES

[Patent Literature 1]: WO 2007/123147
[Patent Literature 2]: JP-A 2003-180649
[Patent Literature 3]: JP-A 2004-000636
[Patent Literature 4]: JP-A 2006-320425

DISCLOSURE OF THE INVENTION

Problems to be Solved by the Invention

However, all of the conventional transcranial magnetic stimulators including devices and systems for coil positioning as described above are intended to be used in a relatively large-scale hospital or a research institute for an examination or a research by skillful specialized physicians. Accordingly, such devices are complicated in handling and operation, require a lot of skill to use, and are quite large-scaled and expensive. For this reason, it is generally difficult for a patient, a family member of the patient, or the patient s personal doctor in the neighborhood who is not necessarily an expert at the magnetic stimulation to perform a treatment by operating the stimulator. In addition, in order to install the stimulator at the patient s own house, a relatively small-scale doctor s office, a clinic, or such, the cost is too much and it is also generally difficult to secure an installation space.

Therefore, patients taking the transcranial magnetic stimulation treatment have no choice but to visit a large hospital having a large-scale magnetic stimulator installed and skillful specialized physicians every time taking the treatment, or to stay in the hospital, and are forced to bear a large burden in various aspects in order to take the treatment continuously and repeatedly.

The present invention is made in view of the above problems, and an object of the present invention is fundamentally to provide a smaller and less expensive magnetic stimulator that can be easily handled and operated and allows a patient to perform a transcranial magnetic stimulation treatment continuously and repeatedly on a daily basis at home, a personal doctor s office in the neighborhood, or such.

Means for Solving the Problems

Thus, a magnetic stimulator according to the present invention is capable of applying magnetic stimulation to a particular portion of a subject, and provided with a) a magnetic field generating means including at least a dynamic magnetic field generating means configured to generate a dynamic magnetic field so as to apply the magnetic stimulation, b) an operating means operated to displace a relative position of the magnetic field generating means with respect to the particular portion of the subject, c) a plurality of magnetic field detecting means each configured to detect the magnetic field generated by the magnetic field generating means, and d) an instructing means configured to provide instruction information based on a result of the detection of the magnetic field generated by the magnetic field generating means, the instruction information indicating an operation of displacement to be performed using the operating means, the detection being made by the magnetic field detecting means either before or during the magnetic stimulation.

Further, another magnetic stimulator according to the present invention is capable of applying magnetic stimulation to a particular portion of a subject, and provided with a) a magnetic field generating means including at least a dynamic magnetic field generating means configured to generate a dynamic magnetic field so as to apply the magnetic stimulation, b) a holding means configured to hold the magnetic field generating means near the particular portion of the subject, c) a plurality of magnetic field detecting means each configured to detect the magnetic field generated by the magnetic field generating means, and d) an instructing means configured to provide instruction information based on a result of the detection of the magnetic field generated by the magnetic field generating means, the instruction information indicating a body movement that the subject is to take in order to apply magnetic stimulation to the particular portion, the detection being made by the magnetic field detecting means either before or during the magnetic stimulation.

In the above cases, it is preferable to further include a fixing means configured to fix the magnetic field detecting means to a predetermined relative position with respect to the particular portion of the subject.

Moreover, it is preferable that the magnetic field generating means is attached to the operating means.

In the above cases, the instructing means is able to generate and provide the instruction information by calculating a position of the magnetic field generating means as a position of a magnetic field source obtained based on an inverse analysis method using information relating to an intensity and a direction of the magnetic field detected by the plurality of magnetic field detecting means. It should be noted that it is possible to use a random walk search method when employing the inverse analysis method.

Alternatively, it is possible to further provide a recording means configured to have information relating to a position of the magnetic field generating means and a piece of information relating to an intensity and a direction of the magnetic field detected by each magnetic field detecting means previously recorded therein in pairs for a plurality of positions at least at this position, and the instructing means can generate and provide the instruction information by calculating a position of the magnetic field generating means based on comparison between the information relating to an intensity and a direction of the magnetic field and the information recorded in the recording means, the intensity and the direction of the magnetic field being detected by each magnetic field detecting means either before or during the magnetic stimulation.

Alternatively, it is possible to further provide a target information recording means having a plurality of pieces of information relating to an intensity and a direction of the magnetic field previously recorded therein, the magnetic field being detected by the magnetic field detecting means in a state in which each magnetic field generating means is positioned either at a position at which the magnetic stimulation is to be applied to the particular portion of the subject or within an allowable range near this position, and the instructing means can generate and provide the instruction information based on a result of comparison between the information relating to an intensity and a direction of the magnetic field and the information recorded in the target information recording means, the intensity and the direction of the magnetic field being detected by each magnetic field detecting means either before or during the magnetic stimulation.

Moreover, it is possible to configure the recording means so as to be capable of recording information of the position of the magnetic field generating means as pieces of position information in a plurality of different coordinate systems, and to include a coordinate converting means capable of performing the comparison by matching the pieces of position information in the plurality of different coordinate systems with each other.

Furthermore, it is possible to configure the instructing means so as to provide instruction information, when applying magnetic stimulation to the particular portion of the subject for treatment, based on a deviation at the particular portion between reference magnetic field data corresponding to at least a position (more preferably, corresponding to the position and posture) of the dynamic magnetic field generating means and the magnetic field data detected by the magnetic field detecting means while operating the magnetic field generating means, the instruction information indicating an operation of displacement to be performed using the operating means.

In this case, it is possible to configure a reference data set as a set of the reference magnetic field data and reference data of at least the position corresponding to the reference magnetic field data, and to configure the instructing means so as to compare magnetic field data based on a result of the detection by the magnetic field detecting means corresponding to at least the position of the dynamic magnetic field generating means with the magnetic field data of a plurality of data sets including the reference data set, and to provide the instruction information indicating the operation of displacement to be performed using the operating means based on the position data of the data set in which a difference between the both magnetic field data is minimized.

In this case, the plurality of data sets other than the reference data set can be obtained separately from the reference data set.

In the above cases, it is possible to configure such that the magnetic field generating means generates a dynamic magnetic field and a static magnetic field.

Alternatively, it is possible to configure such that the magnetic field generating means generates only a dynamic magnetic field.

Further, it is possible to configure such that the magnetic field detecting means detects the dynamic magnetic field and the static magnetic field generated by the magnetic field generating means. In this case, it is possible to configure such that the magnetic field detecting means detects the static magnetic field generated by the magnetic field generating means in a state in which the generation of the dynamic magnetic field by the magnetic field generating means is prevented.

Alternatively, it is possible to configure such that the magnetic field detecting means detects only the dynamic magnetic field generated by the magnetic field generating means.

Moreover, another aspect of the magnetic stimulator according to the present invention is capable of applying magnetic stimulation to a particular portion of a subject, and provided with a) a dynamic magnetic field generating means configured to generate a dynamic magnetic field so as to apply the magnetic stimulation, b) an operating means having a magnetic field generating means including at least the dynamic magnetic field generating means, and displaceably operated with respect to the particular portion of the subject, c) a plurality of magnetic field detecting means each configured to detect the magnetic field generated by the magnetic field generating means, d) a fixing means configured to fix the position of the magnetic field detecting means with respect to the position of the particular portion of the subject, e) a magnetic field analyzing means configured to perform the inverse analysis to the magnetic field generated by the magnetic field generating means based on detection signals from the plurality of magnetic field detecting means to obtain three-dimensional data of the magnetic field generating means, f) a data storing means configured to store desired three-dimensional reference data of the magnetic field generating means, g) a comparing means configured to compare the three-dimensional data obtained by the magnetic field analyzing means with the three-dimensional reference data, and h) an instructing means configured to provide instruction information based on a result of the comparison by the comparing means, the instruction information indicating an operation of displacement of the operating means according to deviation of the three-dimensional data from the three-dimensional reference data.

It should be noted that examples of the desired three-dimensional reference data of the magnetic field generating means include three-dimensional data of the magnetic field generating means corresponding to the optimum position and posture at which the magnetic stimulation is to be applied in the particular portion of the subject.

In the above cases, it is possible to configure such that the operating means only includes the dynamic magnetic field generating means as the magnetic field generating means, and that the magnetic field detecting means detects the dynamic magnetic field generated by the dynamic magnetic field generating means.

Alternatively, instead of this, it is possible to configure such that the operating means includes the dynamic magnetic field generating means and a static magnetic field generating means as the magnetic field generating means, and that the magnetic field detecting means detects the static magnetic field generated by the static magnetic field generating means in a state in which the generation of the dynamic magnetic field by the dynamic magnetic field generating means is prevented.

Further, the three-dimensional reference data can be obtained using a dedicated positioning device external to the magnetic stimulator. Examples of the dedicated positioning device external to the stimulator include, for example, an optical tracking system. Such a positioning device is required only for collecting the reference data.

Alternatively, instead of this, it is possible to configure such that the three-dimensional reference data is obtained using the magnetic field analyzing means of the magnetic stimulator.

When performing the inverse analysis of the magnetic field generated by the magnetic field generating means, it is preferable that the magnetic field analyzing means perform the inverse analysis of the magnetic field employing the random walk search method.

In the above invention, as the instructing means that provides the instruction information, the instructing means that provides at least one of visual information and auditory information is suitable.

In particular, when the instructing means provides the instruction information as the auditory information, it is preferable to provide the instruction by changing at least one of a volume level, a musical scale, and a tone according to either an amount of displacement to be performed by the operating means or an amount of body movement to be made by the subject.

Alternatively, when the instructing means provides the instruction information as the visual information, it is preferable to provide the instruction by changing a color of instruction according to either an amount of displacement to be performed by the operating means or an amount of body movement to be made by the subject.

Further, as the fixing means, a pair of eyeglasses, a pair of earpieces, a pair of headphones, or a headband is suitably used.

The magnetic stimulator as described above can be used as a stimulator that applies the magnetic stimulation to at least a particular portion of the subject s brain for a transcranial magnetic stimulation treatment.

Effects of the Invention

According to the present invention, the instructing means provides the instruction information based on the result of the detection of the magnetic field generated by the magnetic field generating means, the instruction information indicating the operation of displacement to be performed using the operating means, the detection being made by the magnetic field detecting means either before or during the magnetic stimulation.

Therefore, the user of this stimulator can perform the operation of displacement to be performed using the operating means only by operating based on the instruction information provided by the instructing means without needing any special proficiency as conventionally required. Specifically, the patient or the family member of the patient, or a personal doctor in the neighborhood who is not necessarily specialized, can operate and use the stimulator fairly easily. Further, as it is not necessary to use a large-scale and expensive stimulator as conventionally required, the cost can be minimized, and it is easily possible to secure an installation space even in such as the patient s house, or a relatively small-scale doctor s office or clinic.

Specifically, according to the present invention, it is possible to provide the magnetic stimulator that can be easily handled and operated and is further downsized with lower cost, and this allows the patient to perform the transcranial magnetic stimulation treatment continuously and repeatedly on a daily basis at home, the personal doctor s office in the neighborhood, or such.

Moreover, according to the magnetic stimulator of another aspect of the present invention, the magnetic stimulator is provided with the magnetic field analyzing means that performs the inverse analysis of the magnetic field generated by the magnetic field generating means attached to the operating means based on the detection signals from the plurality of magnetic field detecting means, and that obtains the three-dimensional data of the magnetic field generating means. The three-dimensional data obtained by the magnetic field analyzing means is compared with the three-dimensional reference data by the comparing means, and the instruction information indicating the operation of displacement of the operating means according to the deviation of the three-dimensional data from the three-dimensional reference data is provided by the instructing means based on the comparison result.

Therefore, only by manipulating the operating means to displace such that the deviation provided by the instructing means becomes zero based on the instruction information, the user of the stimulator can fairly easily detect the three-dimensional position and posture of the magnetic field generating means corresponding to the required three-dimensional reference data (that is, corresponding to the optimum position and posture at which the magnetic stimulation is to be applied) of the magnetic field generating means, without needing any special proficiency as conventionally required. Specifically, the patient or the family member of the patient, or a personal doctor in the neighborhood who is not necessarily specialized, can operate and use the stimulator fairly easily. Further, as it is not necessary to use a large-scale and expensive stimulator as conventionally required in order to detect the three-dimensional position and posture of the magnetic field generating means, the cost can be minimized, and it is easily possible to secure an installation space even in such as the patient s house, or a relatively small-scale doctor s office or clinic. In this manner, it is possible to provide the magnetic stimulator that can be easily handled and operated and is further downsized with lower cost, and this allows the patient to perform the transcranial magnetic stimulation treatment continuously and repeatedly on a daily basis at home, the personal doctor s office in the neighborhood, or such.

BRIEF DESCRIPTION OF THE DRAWINGS

FIG. 5 is a flowchart explaining the operation method of the transcranial magnetic stimulator in a home treatment.

FIG. 6 is an explanatory diagram schematically illustrating a forward analysis of a magnetic field of a circular coil.

PREFERRED EMBODIMENTS OF THE INVENTION

One embodiment of the present invention is now described with reference to the drawings.

Figure 1:
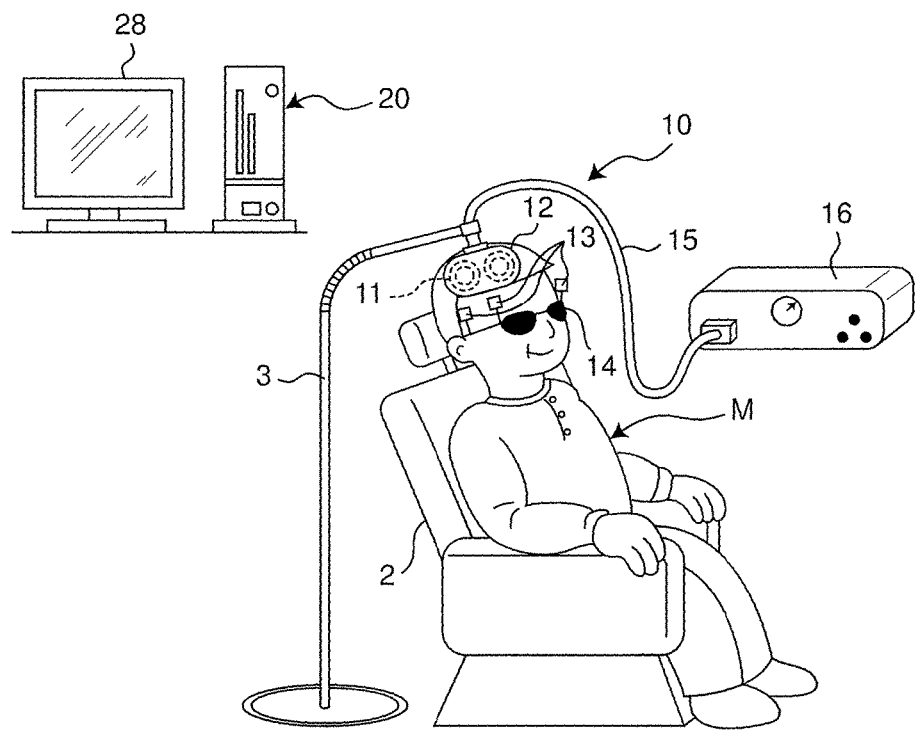
FIG. 1 is an explanatory view schematically illustrating an overall configuration of a transcranial magnetic stimulator according to one embodiment of the present invention.

FIG. 1 is an explanatory view schematically illustrating an overall configuration of a transcranial magnetic stimulator according to this embodiment. In the drawing, a transcranial magnetic stimulator (hereinafter referred to as a magnetic stimulator or simply as stimulator, appropriately) as a whole represented by a reference numeral 10 is intended to perform a treatment and/or relieve symptoms by applying magnetic stimulation to brain nerve using a stimulation coil 11 provided on the surface of a scalp of a patient M (subject) statically seated in a chair 2 for treatment.

The stimulation coil 11 is configured to generate a dynamic magnetic field for applying a magnetic stimulation to a particular portion of the brain of the patient M, and attached to a coil holder 12 that can be manipulated displaceably with respect to a surface of the head of the patient M.

It should be noted that FIG. 1 shows a state in which the coil holder 12 is fixed preferably to a holder fixation member 3 so that the coil 11 does not move unintentionally after the coil 11 has been positioned by displacing the stimulation coil 11 along the patient s scalp while holding the coil holder 12.

Figure 2:
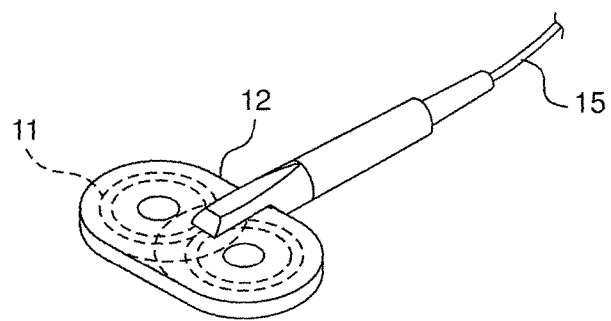
FIG. 2 is a perspective view illustrating one example of a stimulation coil and a coil holder used in the embodiment.

Examples of the stimulation coil 11 to be used include various types of known magnetic coils. FIG. 2 is a perspective view illustrating one example of the stimulation coil and the coil holder capable of being used as a dynamic magnetic field generating means for a transcranial magnetic stimulation treatment according to this embodiment. The stimulation coil 11 shown in FIG. 2 is a so-called figure-eight spiral coil configured by two spiral coils arranged in the figure of eight in the same plane, and its induction current density is maximum immediately under a portion corresponding to an intersection of the figure of eight. The magnetic coil 11 of this type is somewhat difficult to be fixed including determination of its posture, but suitable for applying localized stimulation. The stimulation coil 11 is preferably resin-molded monolithically with the coil holder 12 when molding the coil holder 12 made of synthetic resin.

The stimulation coil 11 is electrically connected to a magnetic stimulation control device 16 via a cable 15. The magnetic stimulation control device 16 is configured to control supply of a current pulse to the stimulation coil 11, and various types of conventionally known devices can be used. ON/OFF manipulation of the magnetic stimulation control device 16 is performed by an operator. Further, setting of intensity and a pulse waveform of the current pulse for determining intensity and a cycle of magnetic stimulation can also be performed by the operator.

In this embodiment, a magnetic field sensor 13 as a magnetic field detecting means capable of detecting a magnetic field generated by the stimulation coil 11 is provided for either side of a frame on left and right of a pair of eyeglasses 14 that the patient M is wearing.

Examples of the sensors 13 to be used include various types of known magnetic field sensors (magnetic sensors) such as an inductive sensor such as a so-called search coil, a Hall sensor utilizing a Hall effect, an MR sensor utilizing a magnetoresistance effect, an MI sensor utilizing a magneto-impedance, and a fluxgate sensor, for example. Many of mass-produced sensors of a few millimeters (mm) square and a few gram (g) can be purchased for about a few hundreds yen per piece. It is possible to obtain sensors that are sufficiently downsized, lightweight, and low-cost as those used in the transcranial magnetic stimulation treatment.

The pair of eyeglasses 14 serves as a fixing means configured to fix positions of the plurality of magnetic field sensors 13 (two, for example, in this embodiment) with respect to the patient s head. The positions at which the magnetic field sensors 13 are to be fixed on the head of the patient M are required to be reproducible, and it is necessary to fix the magnetic field sensors 13 always at the same positions on the patient M. It is desirable to use a familiar appliance (body fitment) that can be frequently worn on a daily basis as a means for fixing the magnetic field sensors 13 on the patient s head in a relatively natural manner without giving a uncomfortable or unpleasant feeling to the patient M while ensuring repeatability and reproducibility of the positions to be fixed. In this point, the pair of eyeglasses 14 is suitable. It should be noted that while a position of a pair of eyeglasses used commonly can be often slightly displaced upward or downward, a so-called pair of protective (safety) glasses and goggles for sporting are designed so as not to easily displaced, and are particularly suitable as an attachment appliance for the magnetic field sensors 13.

The transcranial magnetic stimulator 10 according to this embodiment is provided with a magnetic field analyzing unit 20 capable of, based on detection signals of the plurality of the magnetic field sensors 13, performing an inverse analysis to a detected magnetic field (an intensity and a direction of the magnetic field), calculating and obtaining three-dimensional data of the stimulation coil 11 that has generated the magnetic field as at least a position (preferably the position and a posture) of a source of the magnetic field obtained by the inverse analysis method, and comparing the obtained data with reference data (three-dimensional reference data) that will be later described, thereby sensing deviation (misalignment) from the three-dimensional reference data.

Further, the magnetic field analyzing unit 20 is provided with a display device 28 having a display panel of a liquid crystal type and capable of providing a user (the operator, for example) with the deviation sensed by the unit 20 as visual information.

The display device 28 serves as an interface for, after obtaining a current position (preferably the current position and a current posture) of the stimulation coil 11 by the inverse analysis for a magnetic field, providing the user with the current position (and the current posture) of the coil 11, and guiding the stimulation coil 11 to an optimum position (that is, a position corresponding to an optimum stimulating portion) and an optimum posture. It should be noted that the user in this case refers to the patient, a family member of the patient, a doctor or medical staff at a personal doctor s office and such, for example.

Figure 3:
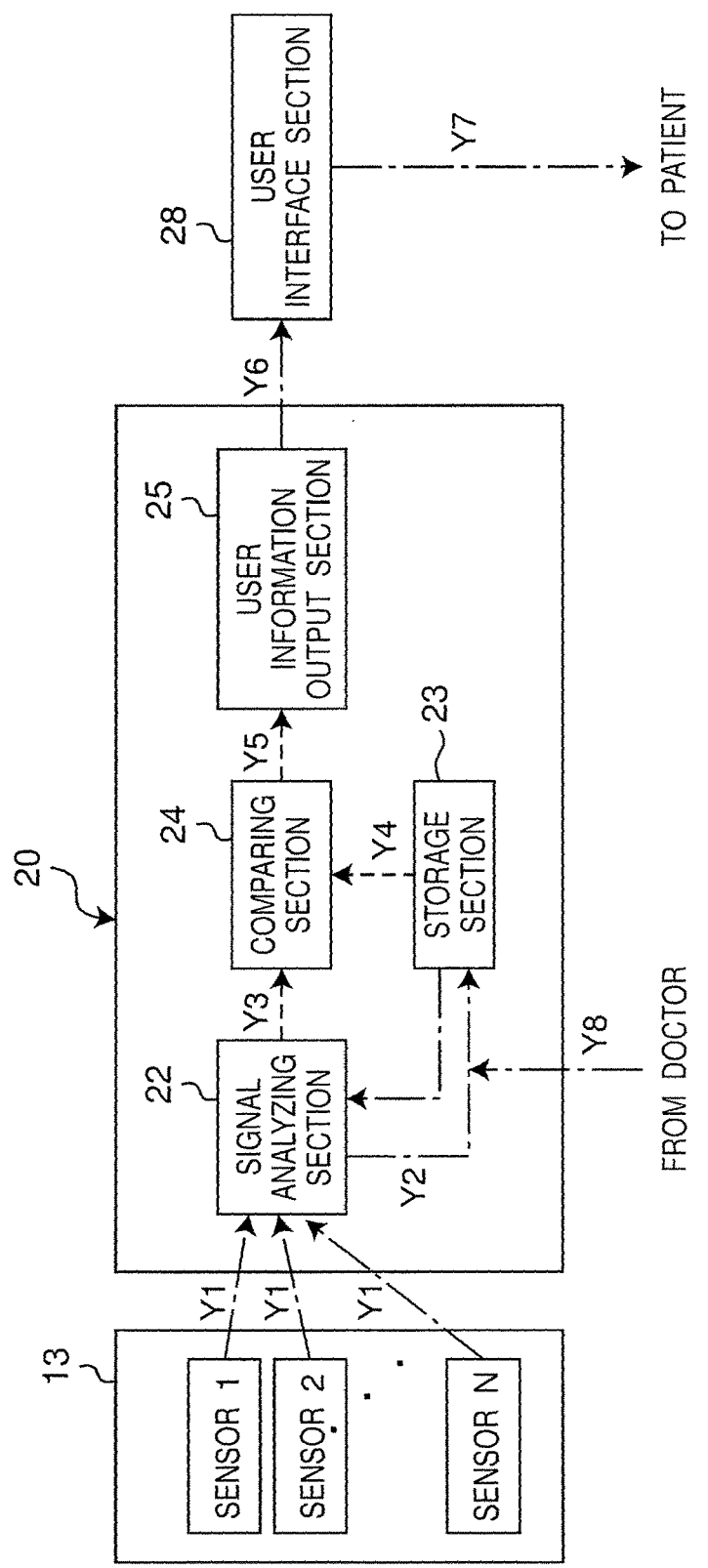
FIG. 3 is a block diagram schematically illustrating a configuration of a magnetic field analyzing unit used in the embodiment.

The magnetic field analyzing unit 20 is configured by a so-called personal computer having a CPU (Central Processing Unit) as a major portion, for example, and as shown in a block diagram of FIG. 3, is provided with a signal analyzing section 22, a storage section 23, a comparing section 24, and a user information output section 25.

The signal analyzing section 22 is configured to, based on detection signals inputted from the plurality of the magnetic field sensors 13 (sensor 1, sensor 2, . . . , and sensor N) that are inputted preferably as wireless signals (see an arrow Y1 in FIG. 3), perform an inverse analysis to the magnetic field generated by the stimulation coil 11, and obtain the three-dimensional data of the stimulation coil 11, that is, the three-dimensional data relating to the position and posture of the stimulation coil 11.

As used herein, the posture of the stimulation coil refers to an orientation and an angle of the stimulation coil 11, the orientation of the stimulation coil refers to a direction to which the coil 11 faces on the surface of the scalp of the patient M, and the angle of the stimulation coil refers to an angle between a normal line of the surface of the scalp of the patient M and a direction of the magnetic field of the coil 11.

Further, the storage section 23 is configured to store the three-dimensional data of the stimulation coil 11 corresponding to the optimum position and posture on the head of the patient M at which the magnetic stimulation is to be applied (that is, the three-dimensional data relating to the position and posture of the stimulation coil 11) as reference data (see an arrow Y2 in FIG. 3). The storage section 23 is configured as a readable memory device.

The three-dimensional reference data represents the optimum position of the coil at which the neuropathic pain of the patient M can be most effectively relieved (so-called sweet spot) and the optimum posture of the coil when applying the magnetic stimulation to the particular portion of the brain of the patient M using the stimulation coil 11, and can be determined using a dedicated positioning device external to the transcranial magnetic stimulator 10 when performing a treatment in the hospital such as in an initial treatment.

Examples of the dedicated positioning device external to the stimulator include an optical tracking system having a conventionally known optical tracking device and a medical image display device (both not depicted), for example, and this positioning device is only required in order to obtain the three-dimensional reference data.

Alternatively, instead of using such a dedicated positioning device external to the stimulator, it is possible to determine the three-dimensional reference data using the magnetic field analyzing unit 20 of the transcranial magnetic stimulator 10 itself, specifically, utilizing the function of the signal analyzing section 22 of the magnetic field analyzing unit 20.

The comparing section 24 is configured to compare the three-dimensional data obtained by the signal analyzing section 22 with the three-dimensional reference data stored in the storage section 23 (see arrows Y3 and Y4 in FIG. 3), and whereby it is possible to sense the deviation (misalignment) of the three-dimensional data obtained by the signal analyzing section 22 from the three-dimensional reference data.

Then, a signal of the deviation data sensed based on a result of the comparison by the comparing section 24 is outputted to a user interface section 28 (the display device in this embodiment) via the user information output section 25 (see arrows Y5 and Y6 in FIG. 3). The user interface section 28 is configured to generate, based on the outputted signal from the user information output section 25, instruction information indicating an operation of displacement to be performed using an operating means (the coil holder 12) (in the case of the display device, a signal for displaying such as a video signal), and provides the user with the generated information.

The operator (user) of the stimulator 10 manipulates the coil holder 12 to displace along the scalp of the patient M while watching the display device 28 (see an arrow Y7 in FIG. 3) such that the deviation shown in a screen of the display device 28 is close to zero (zero) as much as possible. Then, the manipulation of the stimulation coil 11 to displace is stopped at the position and posture of the stimulation coil 11 at which the deviation shown in the screen of the display device 28 is zero (zero) or close to zero as much as possible, and this state is maintained. It should be noted that at this time, as shown in FIG. 1, it is convenient to fix the coil holder 12 using the holder fixation member 3.

An operation method of the transcranial magnetic stimulator 10 thus configured is described with reference to flowcharts of FIG. 4 and FIG. 5, separately in a case of an initial treatment performed by a specialized physician in the hospital, and a case of a home treatment performed by such as the patient M or the family member of the patient M at home.

First, the operation method of the stimulator 10 in the initial treatment performed in a relatively large-scale hospital having a specialized physician is described with reference to the flowchart of FIG. 4.

It should be noted that this hospital is assumed to be provided with the optical tracking system (hereinafter referred to as a reference measuring system as needed) having a conventionally known optical tracking device and the medical image display device (both not depicted) as the dedicated device external to the stimulator for positioning the magnetic stimulation coil 11 used in the transcranial magnetic stimulation treatment at the optimum position (and posture). Using the optical tracking system allows application of the magnetic stimulation to the brain nerve, for example, while visually confirming the target and monitoring the position of the coil and the orientation and the angle with respect to a surface of the brain in real time based on a medical image of the brain of the patient M displayed in the medical image display device (MRI (Magnetic Resonance Imaging) image, for example).

In the initial treatment, upon starting the operation of the stimulator 10, first, in step #11, the patient M wears the sensor unit 13. Specifically, the patient M wears the pair of eyeglasses 14 having the plurality of magnetic field sensors 13 (for example, two, in this embodiment). Along with this, the detection signals are inputted to the signal analyzing section 22 from the plurality of the magnetic field sensors 13 (sensor 1, sensor 2, . . . , and sensor N) (see the arrow Y1 in FIG. 3). Next, in step #12, the doctor searches the optimum position and posture of the stimulation coil 11 while watching the optical tracking device and the medical image display device (both not depicted) and while referring to a response of a muscle in a region where the patient M feels a pain, and whether or not the stimulation coil 11 reaches the optimum position and posture is continuously determined (step #13).

Then, when the stimulation coil 11 reaches the optimum position and posture and the determination result in step #13 becomes YES, by a trigger input from the doctor (switch: ON/see an arrow Y8 in FIG. 3), the position and posture of the stimulation coil 11 is calculated as the three-dimensional data by the signal analyzing section 22 based on the detection signals of the magnetic field sensors 13 inputted at this time (step #14). Specifically, the three-dimensional data in a sensor system (hereinafter referred to as a sensor measuring system as needed) corresponding to the optimum position and posture of the stimulation coil 11 is obtained. Then, as shown by the arrow Y2 in FIG. 3, the three-dimensional data obtained in step #14 is stored in the storage section 23 as the reference data (step #15). In this manner, when setting the three-dimensional reference data in the initial treatment performed in the hospital, none of the comparing section 24, the user information output section 25 and the user interface section 28 is actuated.

Next, the operation method of the stimulator 10 treatment in the home treatment performed at home by such as the patient M or the family member of the patient M is described with reference to the flowchart of FIG. 5. It should be noted that in the home treatment, the three-dimensional reference data is assumed to be stored previously in the storage section 23 of the magnetic field analyzing unit 20 of the transcranial magnetic stimulator 10 based on the initial treatment in the hospital described with reference to the flowchart of FIG. 4. Therefore, in the home treatment, both the trigger input from the doctor represented by the arrow Y8 in FIG. 3 and storage of the three-dimensional reference data in the storage section 23 (see the arrow Y8 in FIG. 3) are not performed.

In the home treatment, upon starting the operation of the stimulator 10, first, in step #21, the patient M wears the sensor unit 13. Specifically, the patient M wears the pair of eyeglasses 14 having the plurality of magnetic field sensors 13 (for example, two, in this embodiment). Along with this, the detection signals are inputted to the signal analyzing section 22 from the plurality of the magnetic field sensors 13 (sensor 1, sensor 2, . . . , and sensor N) (see the arrow Y1 in FIG. 3). Next, in step #22, such as the patient M or the family member of the patient M holds the coil holder 12 and manipulates the stimulation coil 11 to displace along the surface of the scalp of the patient M such that the stimulation coil 11 is close to the optimum position and posture as much as possible.

Corresponding to the displacement of the stimulation coil 11, in step #23, the position and posture of the stimulation coil 11 are calculated by the signal analyzing section 22 as the three-dimensional data. The three-dimensional data obtained by the calculation by the signal analyzing section 22 is compared with the three-dimensional reference data stored in the storage section 23 by the comparing section 24 (see the arrows Y3 and Y4 in FIG. 3). With this, it is possible to sense the deviation (misalignment) of the three-dimensional data obtained by the signal analyzing section 22 from the three-dimensional reference data. Then, the signal of the deviation data sensed based on the result of the comparison by the comparing section 24 is outputted to the user interface section 28 (the display device in this embodiment) via the user information output section 25 (see the arrows Y5 and Y6 in FIG. 3).

Such as the patient M or the family member of the patient M manipulates the coil holder 12 to displace along the scalp of the patient M while watching an image displayed in the display device 28 (see the arrow Y7 in FIG. 3) such that the deviation shown in the screen is close to zero (zero) as much as possible. Specifically, the patient M or the family member of the patient M is navigated to the optimum position and posture of the stimulation coil 11 by the user interface section 28 (display device) (step #24).

At this time, by configuring such that a color of the image displayed in the display device 28 sequentially changes, for example, from blue to yellow, and further to red, according to a magnitude of the deviation of the three-dimensional data obtained by the signal analyzing section 22 from the three-dimensional reference data (an amount of displacement to be made by the coil holder 12), that is, as the stimulation coil 11 moves closer to the optimum position and as the deviation becomes smaller, it is possible to facilitate guidance to the optimum position and posture of the stimulation coil 11, and to further improve user-friendliness.

Then, in step #25, it is determined whether or not the stimulation coil 11 reaches the optimum position and posture, and the steps in step #22 and after are repeatedly executed while the determination result is NO. Subsequently, when the deviation shown in the screen of the display device 28 becomes zero or close to zero as much as possible and the determination result in step #25 becomes YES, the manipulation of the stimulation coil 11 to displace is stopped at the position and posture of the stimulation coil 11 at this time, and this state is maintained. At this time, as described previously, it is convenient to fix the coil holder 12 using the holder fixation member 3 (see FIG. 1).

As described above, according to this embodiment, there is provided the signal analyzing section 22 (magnetic field analyzing means) of the magnetic field analyzing unit 20 that performs the inverse analysis of the magnetic field generated by the stimulation coil 11 (magnetic field generating means) attached to the coil holder 12 (operating means) based on the detection signals from the plurality of the magnetic field sensors 13 (magnetic field detecting means), and obtains the three-dimensional data of the stimulation coil 11. Then, the three-dimensional data obtained by the signal analyzing section 22 is compared with the three-dimensional reference data stored in the storage section 23 by the comparing section 24 (comparing means), and the deviation of the three-dimensional data from the three-dimensional reference data is provided by the user interface section 28 (instructing means) based on the comparison result.

Therefore, only by manipulating the coil holder 12 to displace such that the deviation provided by the user interface 28 becomes zero (zero), the user (user) of the magnetic stimulator 10 can fairly easily detect the three-dimensional position and posture of the stimulation coil 11 corresponding to the required three-dimensional reference data (that is, corresponding to the optimum position and posture with which the magnetic stimulation is to be applied) of the stimulation coil 11, without needing any special proficiency as conventionally required. Specifically, the patient M or the family member of the patient M, or a personal doctor in the neighborhood who is not necessarily specialized, can operate and use the stimulator fairly easily. Further, as it is not necessary to use a large-scale and expensive stimulator as conventionally required in order to detect the three-dimensional position and posture of the stimulation coil 11, the cost can be minimized, and it is easily possible to secure an installation space even in such as the patient s house, or a relatively small-scale doctor s office or clinic. Specifically, it is possible to provide the magnetic stimulator 10 that can be easily handled and operated and is further downsized with lower cost, and this allows the patient M to perform the transcranial magnetic stimulation treatment continuously and repeatedly on a daily basis at home, the personal doctor s office in the neighborhood, or such.

Figure 4:
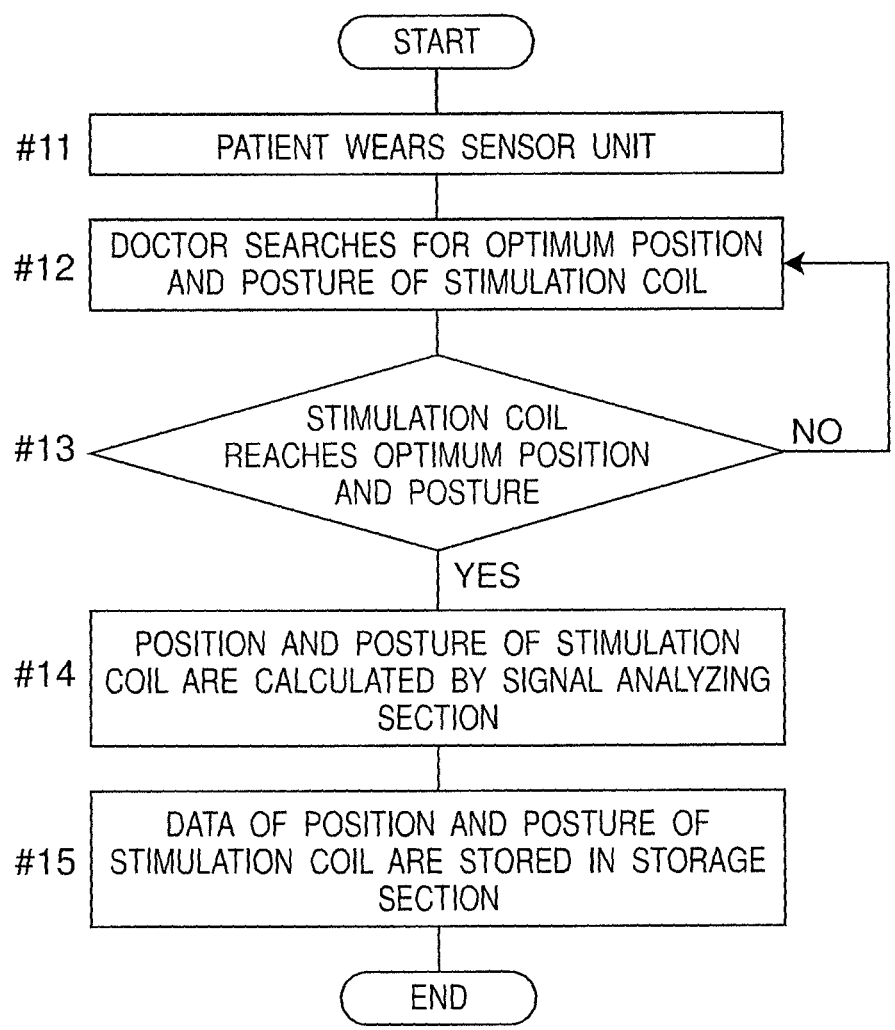
FIG. 4 is a flowchart explaining an operation method of the transcranial magnetic stimulator in an initial treatment performed in a hospital having a specialized physician.

It should be noted that in the description of the operation method, it is assumed that in the process of the initial treatment in the hospital shown in the flowchart of FIG. 4, the doctor performs the step of searching the optimum position and posture of the stimulation coil 11 (FIG. 4: step #12) using a known optical tracking system (reference measuring system). Further, the three-dimensional data in the sensor measuring system corresponding to the optimum position and posture of the stimulation coil 11 determined using the reference measuring system (FIG. 4: step #13) is calculated (FIG. 4: step #14), and the calculated data is stored in the storage section 23 as the three-dimensional reference data (FIG. 4: step #15). However, registration between the sensor system (sensor measuring system) attached to the patient M and the optical tracking system (reference measuring system) can be easily done as described later. Therefore, in a simpler method, the calculation of the three-dimensional data in the sensor measuring system corresponding to the optimum position and posture of the stimulation coil 11 in step #14 of FIG. 4 is unnecessary, and the three-dimensional data of the optimum position and posture of the stimulation coil 11 determined in the reference measuring system can be stored as it is in the storage section 23.

Even with such a configuration, the three-dimensional data of the optimum position and posture of the stimulation coil 11 determined by the doctor in the reference measuring system can be converted into the sensor measuring system by a simple coordinate conversion, and can be used as the three-dimensional reference data in the home treatment without any problem.

However, in a case in which it is necessary to consider an error that can occur in the coordinate conversion, as shown insteps #14 and #15 of FIG. 4, it is still necessary to calculate the three-dimensional data in the sensor measuring system, and to store the calculated data in the storage section 23 as the three-dimensional reference data.

It should be noted that examples of the registration include various known methods, and one example of such methods is described below. For example, when performing a coordinate conversion from a coordinate system. B to a coordinate system A, a coordinate conversion matrix can be derived based on the following basic steps, and the coordinate conversion can be performed using the derived matrix.

(1) First, four feature points that can be measured stably and are not in the same plane are determined.

(2) Next, position coordinates of the four feature points in the coordinate system A including: $(x_1, y_1, z_1)$, $(x_2, y_2, z_2)$, $(x_3, y_3, z_3)$, and $(x_4, y_4, z_4)$ are obtained.

(3) Further, position coordinates of the four feature points in the coordinate system B including: $(x_1, y_1, z_1)$, $(x_2, y_2, z_2)$, $(x_3, y_3, z_3)$, and $(x_4, y_4, z_4)$ are obtained.

(4) A coordinate conversion matrix T is calculated based on Formula 1.

$$T = \begin{pmatrix} x_1 & x_2 & x_3 & x_4 \\ y_1 & y_2 & y_3 & y_4 \\ z_1 & z_2 & z_3 & z_4 \\ 1 & 1 & 1 & 1 \end{pmatrix} \begin{pmatrix} X_1 & X_2 & X_3 & X_4 \\ Y_1 & Y_2 & Y_3 & Y_4 \\ Z_1 & Z_2 & Z_3 & Z_4 \\ 1 & 1 & 1 & 1 \end{pmatrix}^{-1} \quad \text{[Formula 1]}$$

(5) As expressed by Formula 2, by applying the coordinate conversion matrix T, the position coordinate (X, Y, Z) of an arbitrary feature point obtained in the coordinate system B can be converted into the position coordinate (x, y, z) in the coordinate system A.

$$\begin{pmatrix} x \\ y \\ z \\ 1 \end{pmatrix} = T \begin{pmatrix} X \\ Y \\ Z \\ 1 \end{pmatrix} \quad \text{[Formula 2]}$$

Now, the reason why the coordinate conversion matrix T can be calculated based on Formula 1. The four feature points in the coordinate system A and the four feature points in the coordinate system B are physically the same points, respectively, and therefore Formula 3 is established.

$$\begin{pmatrix} x_1 & x_2 & x_3 & x_4 \\ y_1 & y_2 & y_3 & y_4 \\ z_1 & z_2 & z_3 & z_4 \\ 1 & 1 & 1 & 1 \end{pmatrix} = T \begin{pmatrix} X_1 & X_2 & X_3 & X_4 \\ Y_1 & Y_2 & Y_3 & Y_4 \\ Z_1 & Z_2 & Z_3 & Z_4 \\ 1 & 1 & 1 & 1 \end{pmatrix} \quad \text{[Formula 3]}$$

As the four feature points that are not in the same plane are selected, there is an inverse matrix of a matrix expressed by Formula 4, and therefore a calculating formula of Formula 1 is obtained by multiplying both sides of Formula 3 by the inverse matrix from right.

$$\begin{pmatrix} X_1 & X_2 & X_3 & X_4 \\ Y_1 & Y_2 & Y_3 & Y_4 \\ Z_1 & Z_2 & Z_3 & Z_4 \\ 1 & 1 & 1 & 1 \end{pmatrix} \quad \text{[Formula 4]}$$

The registration between the sensor system (sensor measuring system, assumed to be the coordinate system A) and the optical tracking system (reference measuring system, assumed to be the coordinate system B) performed using the above method is now described.

(1) First, four feature points that can be measured stably and are not in the same plane are determined on an magnetic field sensor attachment appliance (in this case, the pair of eyeglasses 14, for example).

(2) Next, position coordinates of the four feature points in the coordinate system A including: $(x_1, y_1, z_1)$, $(x_2, y_2, z_2)$, $(x_3, y_3, z_3)$, and $(x_4, y_4, z_4)$ are obtained. In this case, the coordinate system A is a coordinate system fixed for the magnetic field sensor attachment appliance (the pair of eyeglasses 14), and therefore the position coordinates of the four feature points can be obtained based on designed values of the magnetic field sensor fixation member (the pair of eyeglasses 14).

(3) Further, position coordinates of the four feature points in the coordinate system B including: $(x_1, y_1, z_1)$, $(x_2, y_2, z_2)$, $(x_3, y_3, z_3)$, and $(x_4, y_4, z_4)$ are obtained using a three-dimensional position measuring device (optical tracking system) in the hospital.

(4) The coordinate conversion matrix T is calculated based on Formula 1.

(5) As expressed by Formula 2, by applying the coordinate conversion matrix T, the position coordinate (X, Y, Z) of an arbitrary feature point (thus, of the optimum stimulating position) obtained in the coordinate system B (optical tracking system) can be converted into the position coordinate (x, y, z) in the coordinate system A.

Further, in the description of the operation method, it is assumed that in the process of the initial treatment in the hospital shown in the flowchart of FIG. 4, the data stored in the storage section 23 is limited to the three-dimensional reference data in the sensor measuring system corresponding to the optimum position and posture of the stimulation coil 11 determined by the doctor. However, other than this, for example, placing the coil 11 at a position of the head at which the patient M is expected to place the stimulation coil 11 in the home treatment, and by storing a value detected by the sensor and the three-dimensional data of the position and posture of the coil 11 at this time (data obtained by converting data obtained in the reference measuring system into data in the sensor measuring system) in the storage section 23 at the same time, it is possible to improve the speed and/or the accuracy of a signal analyzing program in the home treatment.

It should be noted that in this case, it is possible to facilitate the determination of the position of the head at which the patient M is expected to place the stimulation coil 11 in the home treatment by partitioning the head in a mesh and displaying coordinates.

Moreover, in the description of the operation method, it is assumed that in the process of the initial treatment in the hospital shown in the flowchart of FIG. 4, the doctor performs the step of searching the optimum position and posture of the stimulation coil 11 (FIG. 4: step #12) using a known optical tracking system (reference measuring system). However, it is possible to search the optimum position and posture of the stimulation coil 11 using the magnetic field analyzing unit 20 of the stimulator 10 without using such an optical tracking system.

As has been widely known, the known optical tracking system generally uses an optical marker, but a permanent magnet can be used instead of the optical marker when using the magnetic field analyzing unit 20. Registration between the sensor coordinate and the medical image coordinate can be made in the same manner as normal calibration utilizing the permanent magnet, by applying a magnetic marker instead of a reflective marker to a position on the nose and the ear, performing the inverse analysis by the sensor system, and obtaining a coordinate of a position of the magnetic marker. The registration here can also be performed using the previously described approach.

In the above embodiment, the pair of eyeglasses 14 is used as an attachment appliance for attaching the magnetic field sensors 13. Instead, other body fixings, for example, a pair of earpieces, a pair of headphones, and a headband, can also be used.

Many types of the headband made of various materials and are worn by fitting along the shape of and around the user s forehead are commercially available, and the pair of earpieces and the pair of headphones are worn by closely fitting along the shape of the user s ear are also commercially available. All of these can be suitably used as an attachment appliance for the magnetic field sensors 13.

Further, in the above embodiment, the user interface section 28 as the instructing means for providing the deviation the three-dimensional data obtained by the magnetic field analyzing unit 20 from the three-dimensional reference data is configured by the display device 28 having a liquid crystal type display panel that provides the deviation by the visual information. Instead, or in addition, it is possible to provide the deviation by auditory information using a loudspeaker and such. In this case, by configuring the instructing means to change at least one of a volume level, a musical scale, and a tone according to the magnitude of the deviation (the amount of displacement to be made by the coil holder 12), that is, as the stimulation coil 11 moves closer to the optimum position, it is possible to facilitate guidance to the optimum position and posture of the stimulation coil 11 and to further improve user-friendliness.

Moreover, in the above embodiment, the so-called figure-eight spiral coil that is suitable to generate localized magnetic stimulation is used as the stimulation coil 11. However, in such a case in which a spot to which the magnetic stimulation is to be applied is relatively large (wide), for example, a simple circular coil can be suitably used. The simple circular coil is easily handled in the operation including the determination of the posture of the coil and with which the magnetic field analysis is easily performed.

It should be noted that, the stimulation coil 11 is not limited to what is disclosed in this specification, and various types of coils can be used according to a purpose of the magnetic stimulation, a required intensity of the stimulation, and various other factors.

Furthermore, in the above embodiment, the three-dimensional reference data corresponding to the optimum position and posture of the stimulation coil 11 obtained previously in the initial treatment is compared with the three-dimensional data of the stimulation coil 11 obtained by the inverse analysis for a magnetic field in the home treatment, and the coil 11 is guided to the optimum position and posture by the navigation of the visual information or the auditory information according to the deviation of the latter from the former. However, instead of obtaining the three-dimensional data from the magnetic field information and comparing the data in this manner, it is possible to guide the coil 11 to the optimum position and posture by directly comparing the pieces of the magnetic field information.

For example, as described above, it is possible to search the optimum position and posture of the stimulation coil 11 using the magnetic field analyzing unit 20 of the stimulator 10 without using the optical tracking system. Then, the magnetic field data to be a reference obtained by the magnetic field sensors 13 in this initial treatment and the magnetic field data obtained by the magnetic field sensors 13 in the home treatment are directly compared without being converted into the three-dimensional data, and the coil 11 is guided such that the magnetic field data of the latter (in the home treatment) becomes as close as possible to the magnetic field data of the former (in the initial treatment) until the latter becomes substantially identical to the magnetic field data of the former. With this, it is possible to guide the coil 11 to the optimum position and posture using the magnetic field information as it is without knowing actual three-dimensional position and posture of the coil 11.

Further, in the above embodiment, the magnetic field sensor 13 as the magnetic field detecting means detects the magnetic field generated by the stimulation coil 11 as the dynamic magnetic field generating means attached to the coil holder 12 as the operating means. However, in addition to the stimulation coil 11, it is possible to provide a permanent magnet as a static magnetic field generating means for the coil holder 12 (operating means), and to use the permanent magnet exclusively for positioning. In this configuration, the magnetic field sensor 13 also detects a static magnetic field in addition to the dynamic magnetic field.

In this case, by detecting the static magnetic field generated by the permanent magnet in a state in which the dynamic magnetic field generated by the stimulation coil 11 is stopped, it is possible to correctly detect a signal for positioning from the static magnetic field generated by the permanent magnet avoiding an interference of the dynamic magnetic field. In particular, in the transcranial magnetic stimulation treatment, as the generation and stopping of the dynamic magnetic field are intermittently repeated during the treatment, it can be considered to turn the magnetic field sensors ON in synchronization with timing of stopping the dynamic magnetic field. However, by providing a plurality of magnetic field sensors having different sensitivities, it is also possible to detect the static magnetic field (permanent magnet) to perform the magnetic field analysis without stopping the generation of the dynamic magnetic field during the treatment and such.

Moreover, as the dynamic magnetic field generates momentary pulses (10 times per second, for example) during the stimulation (during the treatment), it can be considered to switch the magnetic field sensors between ON and OFF in synchronization with timing of the pulse. By turning the magnetic field sensors OFF during the generation of the pulse, it is possible to avoid the interference of the dynamic magnetic field, and it is not necessary to provide a plurality of magnetic field sensors having different sensitivities in this case.

Furthermore, even in the case in which both of the positioning of the coil and the treatment by the magnetic stimulation are performed only using the dynamic magnetic field without using the static magnetic field, it is possible to perform fine adjustment of the position of the coil while performing the magnetic stimulation treatment by generating a relatively weak dynamic magnetic field and positioning the coil prior to the magnetic stimulation treatment, and then generating a relatively strong dynamic magnetic field. In this case, the magnetic field sensor 13 is required to detect two types of dynamic magnetic fields including the relatively weak dynamic magnetic field and the relatively strong dynamic magnetic field.

As can be seen from the above description, the types of the magnetic fields to be detected by the magnetic field sensor includes three types of magnetic fields having different magnetic field intensities.

(a) The relatively weak dynamic magnetic field (generated prior to the magnetic stimulation treatment).

(b) The relatively strong dynamic magnetic field (generated mainly for the magnetic stimulation treatment).

(c) The static magnetic field by the permanent magnet (introduced exclusively for the positioning).

It is practically impossible to detect such magnetic fields having different magnetic field intensities when identical magnetic field sensors are used. In such a case, it is advantageous to provide a plurality of magnetic field sensor groups having different magnetic field intensities as listed below, for example.

(1) A magnetic field sensor group for detecting a permanent magnet marker for positioning to match the medical image information in the initial treatment in the hospital, for example, as described above; this magnetic field sensor group detects the static magnetic field of (c).

(2) A magnetic field sensor group for positioning the coil prior to the magnetic stimulation treatment in the use at home; this magnetic field sensor group detects the relatively weak dynamic magnetic field of (a) or the static magnetic field of (c).

(3) A magnetic field sensor group for fine adjustment of the position of the coil in the magnetic stimulation treatment in the use at home; this magnetic field sensor group detects the relatively strong dynamic magnetic field of (b) or a composite magnetic field of (b) and (c).

Providing the plurality of magnetic field sensor groups having different sensitivities as described above allows positioning of the coil by detecting the magnetic fields having different magnetic field intensities with each other without changing a principle or a specific algorithm for the coil position detection at all.

Next, the method of determining the three-dimensional position of the stimulation coil 11 performed by the signal analyzing section 22 of the magnetic field analyzing unit 20 is described.

Figure 7:
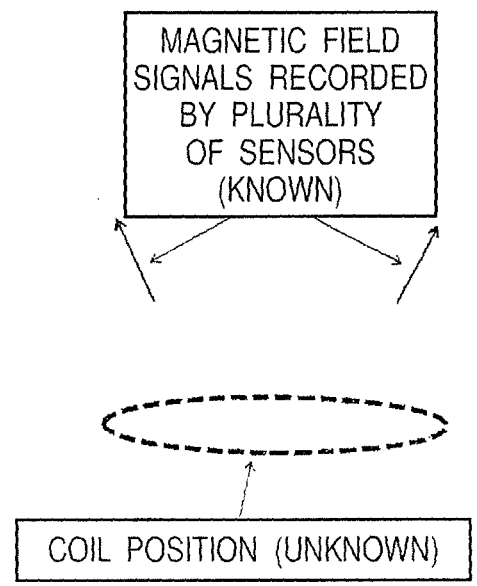
FIG. 7 is an explanatory diagram schematically illustrating an inverse analysis of a magnetic field of the circular coil.

In order to determine the three-dimensional position of the stimulation coil 11, the inverse analysis for a magnetic field is necessary, and the inverse analysis for a magnetic field requires a forward analysis for a magnetic field. As has been widely known, in the forward analysis for a magnetic field, the position of the magnetic field generating source is known and a magnetic field signal at an arbitrary place is analyzed (see FIG. 6). By contrast, in the inverse analysis for a magnetic field, magnetic field signals in a plurality of certain places are known and the position of the magnetic field generating source is analyzed (see FIG. 7).

<Method of Forward Analysis for Magnetic Field>

First, a method of the forward analysis for a magnetic field is described taking a case of a simple circular (annular) coil as an example.

Figure 8:
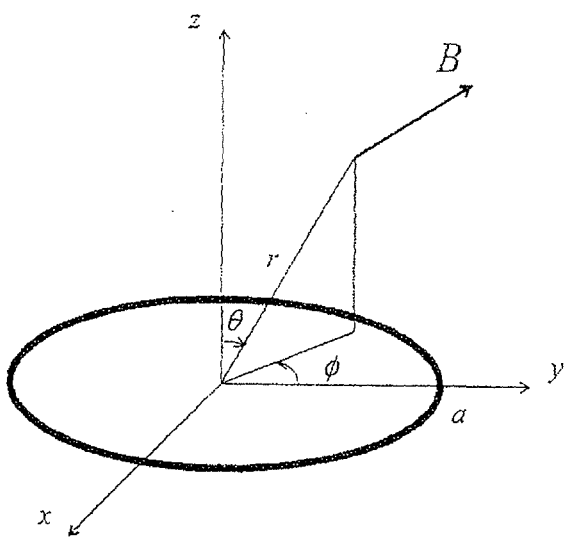
FIG. 8 is an explanatory diagram illustrating a vector relating to an exact solution of the forward analysis of the magnetic field of the circular coil.

As shown in FIG. 8, it is assumed that a circular coil having radius "a" within a plane perpendicular to a z-axis centering an original point, and that a current I flows through the coil. In this condition, vectors of a magnetic field generated by the circular coil respectively in a case of an exact solution and in a case of an approximate solution are as described below. Here, $\mu_0$ is magnetic permeability in vacuum, and a unit is an MKSA unit system.

[In Case of Exact Solution]

Where a vector of a magnetic field at an arbitrary point (r, θ, φ) shown in FIG. 8 is $B=(B_r, B_\theta, B_\phi)$, components by the exact solution are expressed by Formula 5.

Here, $A_\phi$ is a vector potential expressed by Formula 6, K(k) and E(k) respectively are complete elliptic integrals of the first kind and the second kind, and k is expressed by Formula 7.

$$B_r = \frac{1}{r\sin\theta}\frac{\partial}{\partial\theta}(A_\phi\sin\theta),\ B_\theta = -\frac{1}{r}\frac{\partial}{\partial r}(rA_\phi),\ B_{\phi=0} \quad [\text{Formula 5}]$$

$$A_\phi = \frac{\mu_0 I a}{4\pi}\int_0^{2\pi}\frac{\cos\phi'd\phi'}{(a^2+r^2-2ar\sin\theta\cos\phi')^{\frac{1}{2}}} \quad [\text{Formula 6}]$$

$$= \frac{\mu_0}{4\pi}\frac{4Ia}{\sqrt{a^2+r^2+2ar\sin\theta}}\left[\frac{(2-k^2)K(k)-2E(k)}{k^2}\right]$$

$$k^2 = \frac{4ar\sin\theta}{a^2+r^2+2ar\sin\theta} \quad [\text{Formula 7}]$$

<In Case of Approximate Solution>

Figure 9:
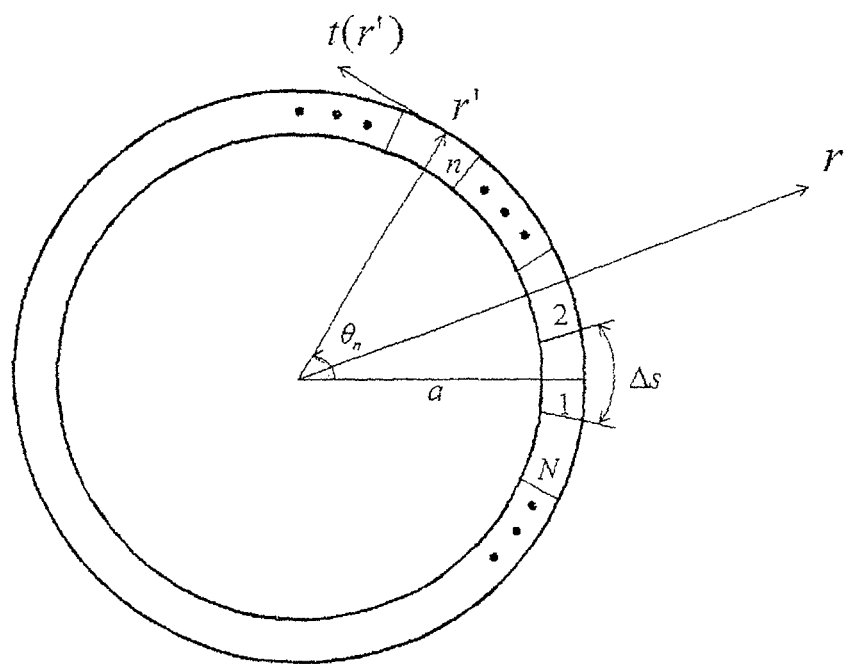
FIG. 9 is an explanatory diagram schematically illustrating a segmentation model for obtaining an approximate solution of the forward analysis of the magnetic field of the circular coil.

When obtaining an approximate solution, as shown in FIG. 9, it is assumed to use a model in which a circular coil in divided into N elements in a circumferential direction, and the divided elements are approximated by straight lines (line segments). In this segmentation model, a magnetic field at a position r generated by an n-th element at a position r is given by the Biot-Savart law expressed by Formula 8. Here, Δs, r, and t(r) in Formula 8 are respectively obtained based on formulas listed below.

Δs=2πa/N t(r)=(−sin θn, cos θn,0)

r=(a·cos θn,a·sin θn,0)

where θn=2πn/N $$\Delta B_n = \frac{\mu_0}{4\pi}\frac{It(r')\times(r-r')}{|r-r'|^3}\Delta s \quad [\text{Formula 8}]$$

The magnetic field generated by the circular coil as a whole is a sum of magnetic field vectors generated by the divided elements, and is expressed by Formula 9 below.

$$B = \sum_{n=1}^{N}\Delta B_n \quad [\text{Formula 9}]$$

A magnetic field distribution approximated based on the above Formulas can be expressed by Formula 10 and Formula 11 listed below.

$$B(x, y, z, a, I) = \begin{bmatrix} B_x \\ B_y \\ B_z \end{bmatrix}$$ [Formula 10]

$$= \sum_{n=1}^{N} K(x, y, z, a, I) \begin{bmatrix} z\cos\theta_n \\ z\sin\theta_n \\ a - x\cos\theta_n - y\sin\theta_n \end{bmatrix}$$

$$K(x, y, z, a, I) = \frac{\mu_0 a I}{2N}((x - a\cos\theta_n)^2 + (y - a\sin\theta_n)^2 + z^2)^{-\frac{3}{2}}$$ [Formula 11]

Figure 10:
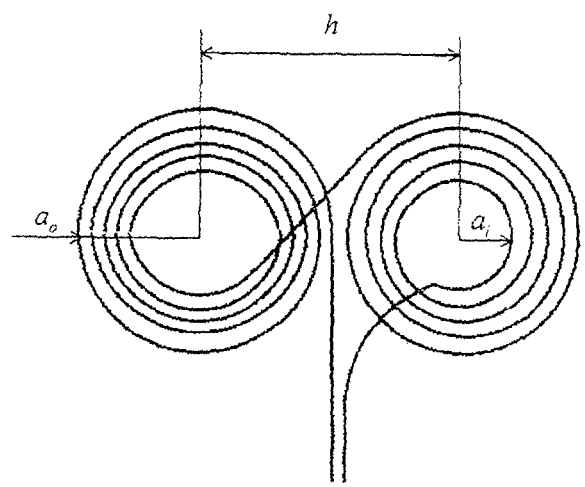
FIG. 10 is an explanatory diagram illustrating a figure-eight spiral coil used in the embodiment.

As described above, the coil used in the magnetic stimulation according to the present embodiment is not a simple circular (annular) coil, and a coil configured by two spiral coils arranged in the figure of eight in the same plane as schematically shown in FIG. 10. It should be noted that the spiral coil can take an angle structure in which the two spiral coils makes a predetermined angle with each other.

Therefore, in this embodiment, the magnetic field distribution is subjected to the forward analysis using the approximate solution that can accommodate a difference in the shape of the coil. As magnetic fields are based on the superposition principle, the magnetic fields generated respectively by the left and right spiral coils in superposition are expressed by Formula 12 listed below. In Formula 12, a first term represents a contribution of a left spiral, and a second term represents a contribution of a right spiral. Further, in Formula 12, "K" represents a number of coil turns, "$a_o$" represents a dimension of an external radius, "$a_i$" represents a dimension of internal radius, and "h" represents a center-to-center distance between the two coils.

$$\begin{bmatrix} B_x \\ B_y \\ B_z \end{bmatrix} = \sum_{k_1=1}^{K} B\left(x - \frac{h}{2}, y, z, \frac{(a_o - a_i)(k_1 - 1)}{K - 1} + a_i, -I\right) +$$

$$\sum_{k_2=1}^{K} B\left(x + \frac{h}{2}, y, z, \frac{(a_o - a_i)(k_2 - 1)}{K - 1} + a_i, -I\right)$$

[Formula 12]

<Method of Inverse Analysis for Magnetic Field>

Next, a method of the inverse analysis for a magnetic field is described. In the present embodiment, in the inverse analysis for a magnetic field for determining the three-dimensional position of the coil from the magnetic field signals, a least-square approach is used, in addition to the forward analysis for a magnetic field expressed by Formula 12.

[Least-Square Approach]

In this case, n nonlinear equations having n variables listed below are assumed.

$f_1(x_1, x_2, \ldots, x_n) = 0$ $f_2(x_1, x_2, \ldots, x_n) = 0$ $f_n(x_1, x_2, \ldots, x_n) = 0$ Here, when expressing a set of the n variables $[x_1, x_2, \ldots, x_n]$ by x, a set of n functions $[f_1(x), f_2(x), \ldots, f_n(x)]$ can be expressed by f(x), and the n nonlinear equations can be expressed as f(x)=0.

As the equation f(x)=0 is a nonlinear equation, a so-called exact solution is not present in most cases. Therefore, some kind of approximation is required to be performed in order to solve the equation. As one example of such approximation, a method of utilizing a magnitude of f(x), that is, $F(x) = \|f(x)\|^2$, and finding an x* value so as to minimize its value is conceivable, instead of solving the equation. It is possible to consider that x* can be taken as the solution if F(x*) is sufficiently close to zero. This method is the so-called least-square approach.

In the present embodiment, provided that a magnetic field read by an α-th sensor is represented as Bα, and that the coil is present at a certain position (whose coordinate is known), the equation is expressed by Formula 13 listed below where a magnetic field at the position of the sensor obtained by the forward analysis is represented by B.

$$f = \sum_{\alpha} \frac{1}{2} |B - B^{\alpha}|^2$$ [Formula 13]

B is updated so as to minimize the value of f, that is the assumed position of the coil. A method of update will be described below.

A hypothetical coil position that gives B when f is minimized is approximated with an actual coil position, and a current coil position (the three-dimensional data) of the stimulation coil can be obtained. Guidance is performed while searching for and updating the coil position, based on the three-dimensional data of the current position, such that the deviation (misalignment) from the optimum position (three-dimensional reference data) determined in the initial treatment becomes zero.

[Coil Position Updating Method 1]

As one method of updating the coil position (that is, a method of search), it is possible to consider utilizing a so-called Trust Region Dogleg Method. As the Newton method has a problem that convergence does not occur based on an initial value, the Trust Region Dogleg method is developed to cover the shortcomings of the Newton method, and ensures global convergence property and is considered to have favorable convergence property. However, it also involves problems that an algorithm is more complex as compared to the Newton method and time for analysis increases.

Figure 11:
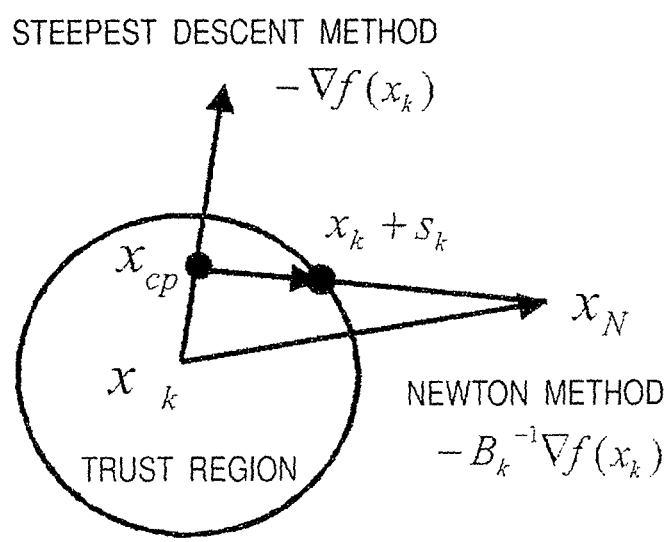
FIG. 11 is an explanatory diagram schematically illustrating a trust region method in a coil position search.

As shown in FIG. 11, the trust region method is constructed by adding a trust region to the Newton method and a steepest descent method.

It is assumed that $B_k$ is taken as a Hessian matrix $\nabla^2 f(x_k)$ or its approximate matrix, a trust radius is taken as $\Delta_k$, a secondary model function $q_k(s_k)$ (constraint condition: $|s_k| \le \Delta_k$) of a formula listed below where $B_k$ is a positive definite is given, and $\Delta_k > 0$ is given.

$$q_k(s_k) = f(x_k) + \nabla f(x_k)^T s_k + \frac{1}{2} \cdot s_k^T B_k s_k$$

At this time, a point obtained as the Newton method is taken as $x_N = x_k - B_k^{-1} \nabla f(x_k)$, and a least point of the secondary model $q_k(s_k)$ when moving along a steepest descent direction $-\nabla f(x_k)$ from a point $x_k$ is taken as $x_{cp}$. The point $x_{cp}$ is referred to as a Cauchy point. If $x_N$ is within the trust region, $x_k + s_k = x_N$. Otherwise, a point that is a piecewise linear point connecting $x_k$, $x_{cp}$, and $x_N$, and whose distance from the point $x_k$ is $\Delta_k$ is selected as $x_k + s_k$ (see FIG. 11). Specifically, when the trust radius is sufficiently large, the Newton method is adopted, and when the trust radius is small, the method considering the steepest descent direction is adopted.

Further, by comparing an amount of reduction of the value of the model function:

$$\Delta q_k = q_k(s_k) - q_k(0) = \nabla f(x_k)^T s_k + \tfrac{1}{2} \cdot s_k^T B_k s_k$$

with an amount of reduction of a value of an objective function:

$$\Delta f_k = f(x_k + s_k) - f(x_k)$$

and the approximate solution is updated as need based on magnitudes of the amounts of reduction (a condition for updating is arbitrary). In addition, a size of the trust region is updated as need depending on the situation at the time.

[Coil Position Updating Method 2]

As an alternative coil position updating method (that is, search method), it is possible to consider utilizing Random Walk (RW) search method.

Figure 12:
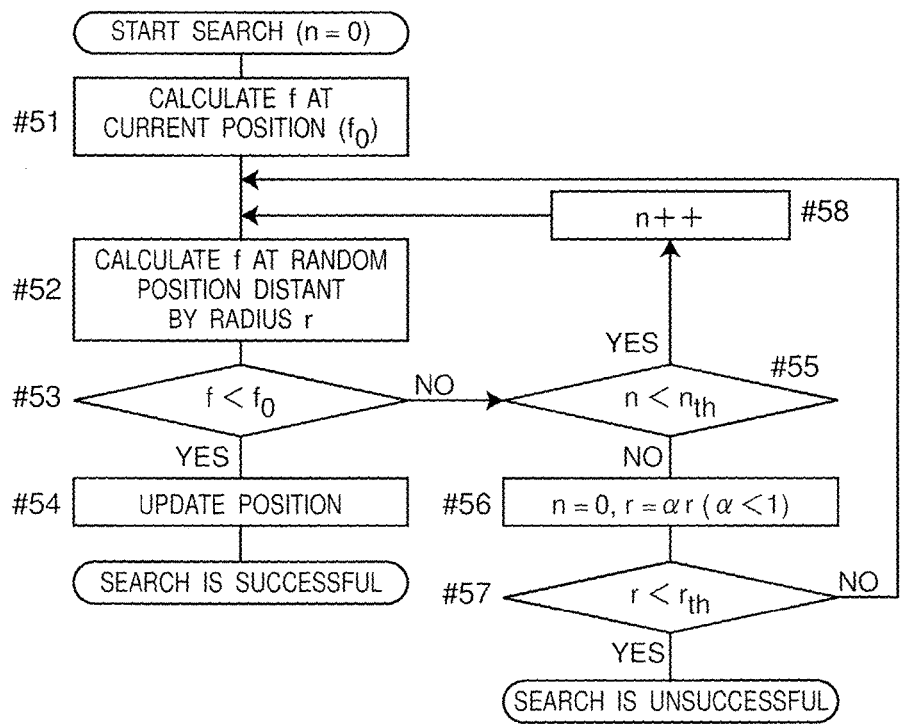
FIG. 12 is a flowchart explaining a random walk search method in a coil position search.

As shown in a flowchart of FIG. 12, for example, the RW method is a method of randomly selecting a position near the hypothetical coil position, calculating the value of "f" based on the least-square approach when the coil is assumed to be moved to this position, and updating the coil position if the value of "f" is improved. The RW method is relatively simple method of gradually making convergent at the correct coil position by repeating the above steps.

Parameters of the RW method shown in the flowchart of FIG. 12 represent facts listed below.

$n_{th}$: an upper threshold of the number of times of radius search (n)

$r_{th}$: a lower threshold of a search radius (r)

$\alpha$: a radius updating parameter (where $\alpha<1$)

In the flowchart of FIG. 12, the number of times of radius search n=0 in an initial state, and when the search is started in this initial state, first, in step #51, the value of f at a hypothetical current coil position is calculated. The value of f at this point (that is, an initial value of f) is taken as $f_0$ ($f=f_0$). Next, in step #52, the value of f at a random position that is distant from the current position in step #51 by the radius r is calculated. Then, in step #53, it is determined whether or not the calculated value f is smaller than the initial value $f_0$ ($f<f_0$). When the determination result in step #53 is YES, as this means that the value of f is improved, the update of the position is performed (step #54). That is, the search is successful.

By contrast, when the determination result in step #53 is NO, in step #55, it is determined whether or not the number of times of radius search n does not reach the upper threshold $n_{th}$ ($n<n_{th}$). If the number of times does not reach the upper threshold (step #55: YES), in step #58, a counting number of the number of times of radius search n is incremented (that is, the counting number n increases only by 1), and the process returns to step #52 and the steps of step #52 and after are repeated. Alternatively, if the determination result in step #55 is NO, the number of times of radius search n has reached the upper threshold $n_{th}$. Therefore, in step #56, the counting number of the number of times of radius search n is reset (n=0) and the search radius r is taken as $\alpha r$ ($r=\alpha r$), and further, in step #57, it is determined whether or not the search radius r reaches the lower threshold $r_{th}$ ($r<r_{th}$). If the determination result in step #57 is NO, the process returns to step #52 and the steps of step #52 and after are repeated. By contrast, if the determination result in step #57 is YES, the search is unsuccessful as the search radius r has reached the lower threshold $r_{th}$.

<Coordinate Conversion>

Figure 13:
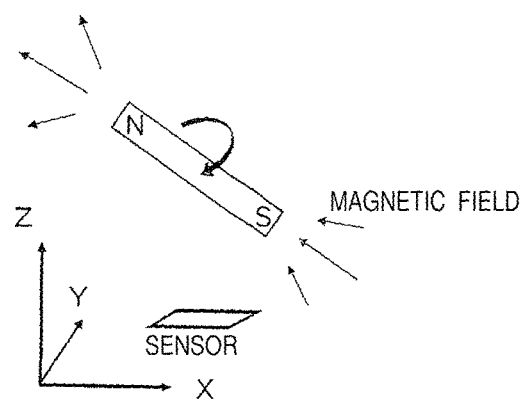
FIG. 13 is an explanatory diagram schematically illustrating a coordinate display when using a permanent magnet.
Figure 14:
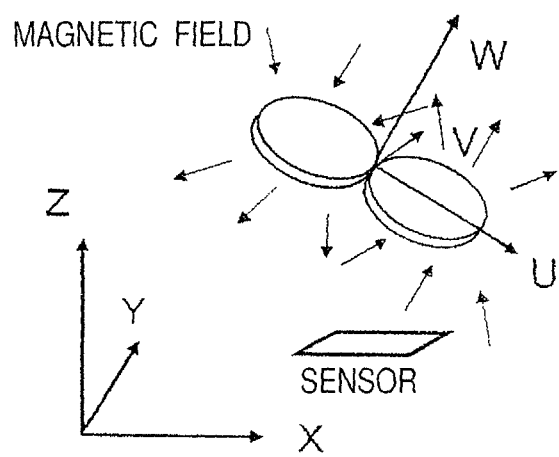
FIG. 14 is an explanatory diagram schematically illustrating a coordinate display when using the figure-eight spiral coil.

As shown in FIG. 13, in a case of the permanent magnet, the magnetic field does not change even if the magnet rotates centering an axis line connecting the north pole and the south pole. However, as shown in FIG. 14, in a case of the figure-eight coil used in this embodiment, the magnetic field sensed by the magnetic field sensors changes if the coil rotates centering any of axes U, V, and W. That is, in the case of the permanent magnet, the inverse analysis can be performed if two coordinates of the north pole and the south pole are known. However, in the case of the figure-eight coil, the inverse analysis cannot be performed unless a coordinate within the plane in which the coil is placed is additionally known. Further, in the case of the figure-eight coil, the forward analysis can be performed only in a coil coordinate system (UVW coordinate system), and therefore it is necessary to perform coordinate conversion of the sensor positions in a new coil coordinate system for every update of the hypothetical coil position. It can be considered that this is a difficult point of the coil inverse analysis for a magnetic field.

Next, the coordinate conversion in the three-dimensional coordinate system required for the coil inverse analysis for a magnetic field.

Figure 15:
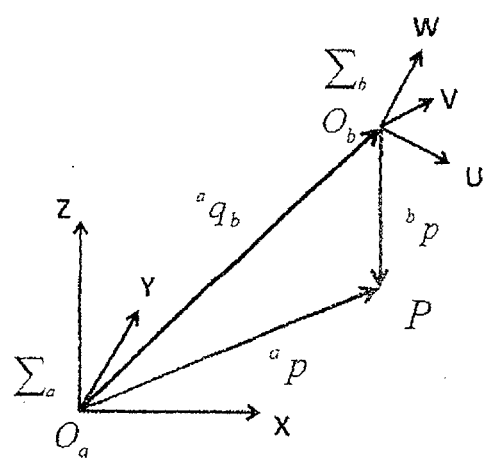
FIG. 15 is a line diagram explaining a coordinate conversion when using the figure-eight spiral coil.

As shown in FIG. 15, it is assumed that two three-dimensional Cartesian coordinate systems $\Sigma_a$ and $\Sigma_b$ are set. Here, it is assumed that a point P expressed in the coordinate system $\Sigma_a$ is $^a p$, the point P expressed in the coordinate system $\Sigma_b$ is $^b p$, and a vector expressing a position vector of an original point in the coordinate system $\Sigma_b$ in the coordinate system $\Sigma_a$ is $^a q_b$. At this time, a relation between $^a p$ and $^b p$ is expressed by a formula listed below.

$$^a p = {}^a R_b \, {}^b p + {}^a q_b$$

Here, $^a R_b$ is a 3×3 matrix, which is referred to as a rotation matrix, expressing a posture in the coordinate system $\Sigma_b$ with respect to coordinate system $\Sigma_a$. As each column vector represents a unit vector of each axis in the coordinate system $\Sigma_b$, a formula below is established.

$$^b R_a = ({}^a R_b)^T = {}^a R_b^{-1}$$

Therefore, a relation between $^a p$ and $^b p$ is also expressed by Formula 14 listed below.

Further, a rotation matrix $^a R_b$ about each of an X axis, a Y axis, and a Z axis, is expressed by Formula 15 when rotating by $\theta$ centering the X axis, expressed by Formula 16 when rotating $$\begin{aligned}
^b p &= ({}^a R_b)^{-1}({}^a p - {}^a q_b) \\
&= ({}^a R_b)^T ({}^a p - {}^a q_b) \\
&= {}^b R_a ({}^a p - {}^a q_b) \\
&= {}^b R_a \, {}^a p + {}^b q_a
\end{aligned}$$

by $\phi$ centering the Y axis, and expressed by Formula 17 when rotating by $\phi$ centering the Z axis, respectively.

[Formula 14]

[Formula 15]

$$^a R_b = \begin{pmatrix} 1 & 0 & 0 \\ 0 & \cos\theta & -\sin\theta \\ 0 & \sin\theta & \cos\theta \end{pmatrix}$$

-continued $$^aR_b = \begin{pmatrix} \cos\phi & 0 & \sin\phi \\ 0 & 1 & 0 \\ -\sin\phi & 0 & \cos\phi \end{pmatrix}$$ [Formula 16]

$$^aR_b = \begin{pmatrix} \cos\psi & -\sin\psi & 0 \\ \sin\psi & \cos\psi & 0 \\ 0 & 0 & 1 \end{pmatrix}$$ [Formula 17]

Using the inverse analysis method as described above, various simulations are carried out.

Next, the inverse analysis simulations are described.

<Simulation 1>

First, as a first step of the simulation, it is examined whether or not the correct coordinate of the coil can be obtained by the inverse analysis, assuming that a so-called single coil whose number of coil turns is one is used for simplification, when the posture of the coil is constant (that is, when the coil coordinate system is parallel translation from an absolute coordinate system. More specifically, a degree that the convergence property varies depending on a difference of the hypothetical coil initial position (that is, dependency of the convergence property on the initial position) is examined, and at the same time, how the convergence property varies depending on the number of the magnetic field sensors is examined. A degree of freedom of the coil is total six: three for the position and three for the posture. Accordingly, theoretically, the two magnetic field sensors are sufficient for performing the inverse analysis. Here, the simulation is carried out to cases in which the number of the sensors is 2, 3, and 4, respectively.

In this simulation, a center position of the actual coil is randomly selected within a cuboid expressed by x=0.90 to 1.10 [m], y=0.90 to 1.10 [m], and z=1.10 to 1.20 [m]. Sensor coordinates are set as expressed by Formula 18, Formula 19, and Formula 20, respectively, for the cases in which the number of the sensors 2, 3, and 4.

$$\begin{pmatrix} x \\ y \\ z \end{pmatrix} = \begin{pmatrix} 0.90 \\ 1.00 \\ 1.00 \end{pmatrix}, \begin{pmatrix} 1.10 \\ 1.00 \\ 1.00 \end{pmatrix}$$ [Formula 18]

$$\begin{pmatrix} x \\ y \\ z \end{pmatrix} = \begin{pmatrix} 0.90 \\ 1.00 \\ 1.00 \end{pmatrix}, \begin{pmatrix} 1.10 \\ 1.00 \\ 1.00 \end{pmatrix}, \begin{pmatrix} 1.00 \\ 1.17 \\ 1.00 \end{pmatrix}$$ [Formula 19]

$$\begin{pmatrix} x \\ y \\ z \end{pmatrix} = \begin{pmatrix} 0.90 \\ 0.90 \\ 1.00 \end{pmatrix}, \begin{pmatrix} 0.90 \\ 1.10 \\ 1.00 \end{pmatrix}, \begin{pmatrix} 1.10 \\ 1.10 \\ 1.00 \end{pmatrix}, \begin{pmatrix} 1.10 \\ 0.90 \\ 1.00 \end{pmatrix}$$ [Formula 20]

Further, an occurrence pattern of the hypothetical coil initial position is set as shown in Table 1.

TABLE 1

| Pattern | Occurrence range of hypothetical coil initial position | The number of sensors |
|---|---|---|
| $S_1$ | Sphere with radius of 0.50 (M) centering point (1.00, 1.00, 1.00) | 2 |
| $S_2$ | Upper hemisphere with radius of 0.50 (M) centering point (1.00, 1.00, 1.00) | 2 |
| $S_3$ | Same as $S_1$ | 3 |
| $S_4$ | Same as $S_2$ | 3 |
| $S_5$ | Same as $S_1$ | 4 |
| $S_6$ | Same as $S_2$ | 4 |

Figure 16:
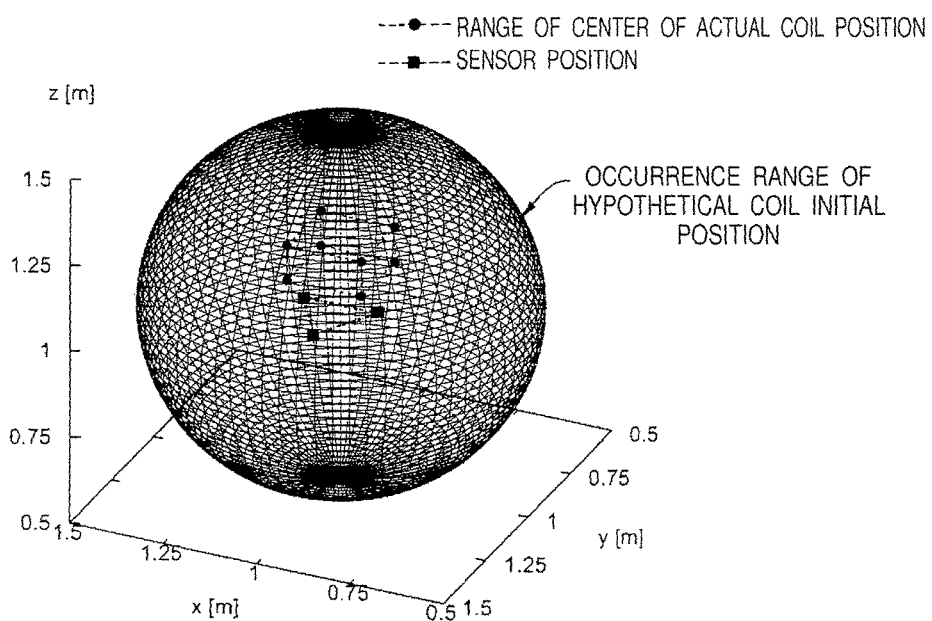
FIG. 16 is an explanatory diagram illustrating one example of positional relation between an occurrence range of an initial position of a hypothetical coil and a position of a sensor in Simulation 1 of the inverse analysis of a single coil.

In FIG. 16, a relation among an occurrence range of the hypothetical coil initial position, a range of the center position of the actual coil, and the positions of the sensors is shown, taking a pattern S3 in Table 1 as an example.

In the update of the position of the hypothetical coil, the convergence property is examined by changing the hypothetical coil initial position 100 times for each pattern using only the trust region method. It should be noted that an upper threshold of the number of times of calculation according to the trust region method in each trial is set to 30 times.

[Result of and Discussion for Simulation 1]

Out of 100 trials, an error closest to the true value (that is, a minimum error) is shown in Table 2. Further, FIG. 17 shows a ratio of the number of trials whose error from the true value is within 10 [cm] out of the 100 trials for each pattern, and FIG. 18 similarly shows a ratio of the number of trials whose error from the true value is within 5 [cm] for each pattern.

TABLE 2

| Pattern | Closest error (cm) |
|---|---|
| $S_1$ | 1.96 |
| $S_2$ | 1.32 |
| $S_3$ | 1.66 |
| $S_4$ | 1.97 |
| $S_5$ | 2.26 |
| $S_6$ | 2.37 |

Figure 17:
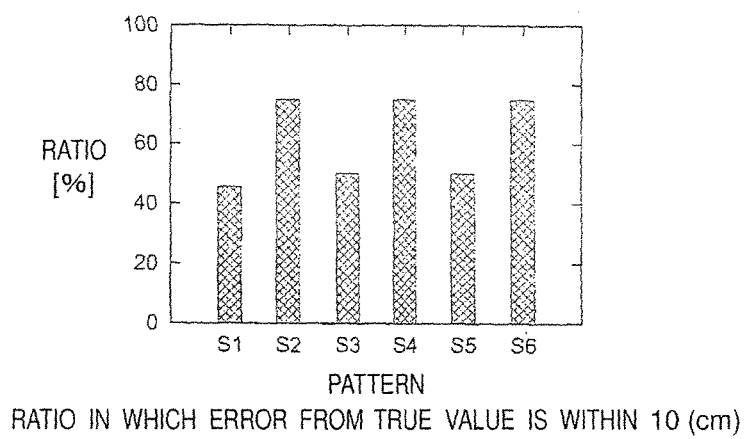
FIG. 17 is a graphical chart showing ratios of the number of trials whose error from a true value is within 10 [cm] in Simulation 1.
Figure 18:
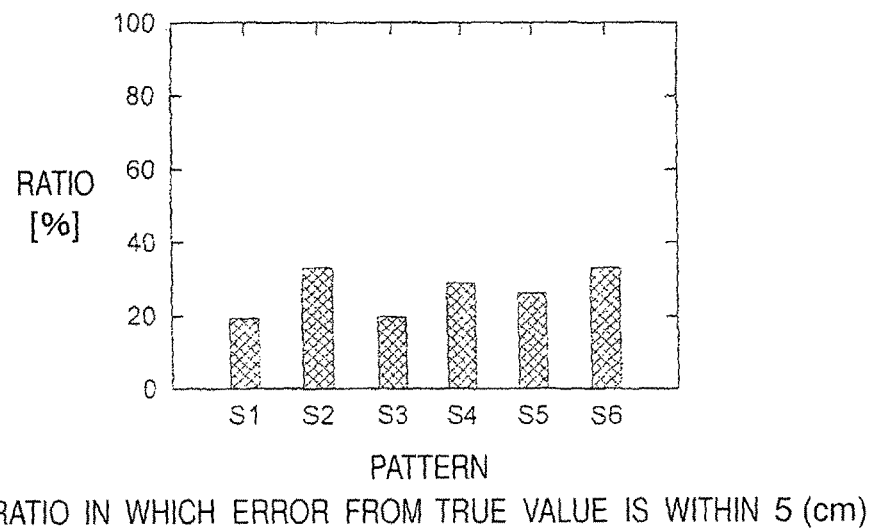
FIG. 18 is a graphical chart showing ratios of the number of trials whose error from a true value is within 5 [cm] in Simulation 1.

Based on data shown in Table 2, FIG. 17, and FIG. 18, it was found that the convergence property is clearly better when the hypothetical coil initial position is started from a position closer to the true value (the patterns S2, S4, and S6) than when the hypothetical coil initial position is started from a position distant from the true value (the patterns S1, S3, and S5). Specifically, the convergence property when performing the inverse analysis for a magnetic field is dependent on the initial position.

However, when the hypothetical coil initial positions are equivalent and the number of sensors are different (the patterns S1, S3, and S5, and the patterns S2, S4, and S6), no influence of the number of sensors to the convergence property was shown in the inverse analysis for a coil magnetic field according to this simulation.

Further, as described above, in each trial, although the upper threshold of the number of times of calculation according to the trust region method is set to 30 times, no significant difference in the error from the true value was shown even if the number of times of calculation was increased. This is considered to be because the value of f takes a local minimum obtained based on the least-square approach at a final point in each trial. That is, it is considered to be because the function f has a plurality of local minimums at positions from the true value by a few centimeters. In the trust region method, increasing the number of times of calculation always makes the solution to converge to the local minimum instead of diverging. However, when the function f has the plurality of local minimums near the true value, the solution disadvantageously converges to one of the local minimums (that is not a global minimum) regardless of a magnitude of the error from the true value.

<Simulation 2>

[Examination of Presence of Local Minimum]

Figure 19:
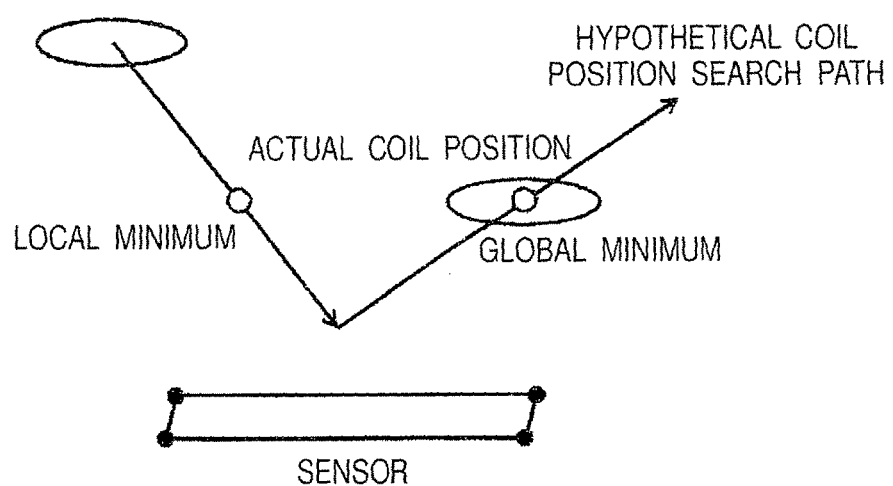
FIG. 19 is an explanatory diagram illustrating one example of a search route of a coil position in Simulation 1.
Figure 20:
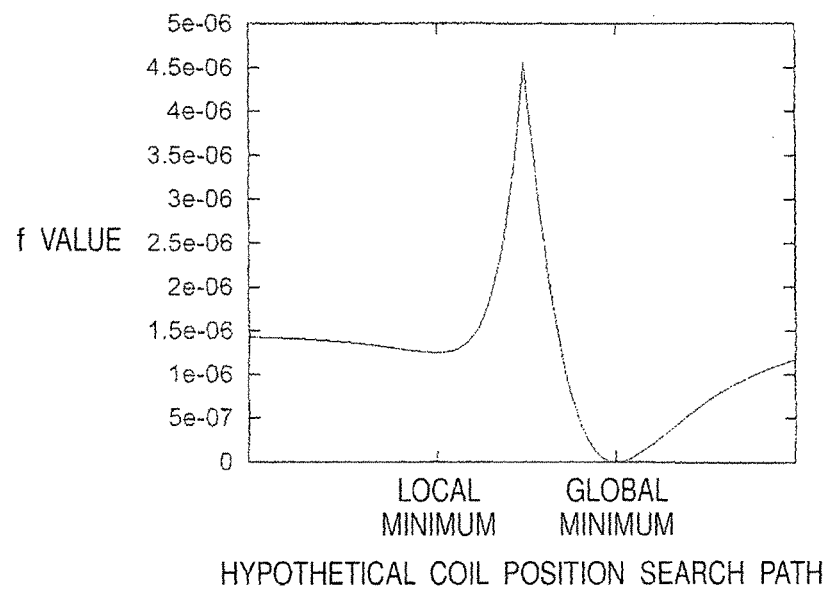
FIG. 20 is a graphical chart showing a local minimum and a global minimum of a function f when passing the search route shown in FIG. 19.

In this embodiment, the magnetic field generated by the coil is weak at a portion distant from the coil by about 4 to 5 [cm] or more, and significantly strong at a position closer than this distance. Therefore, as shown in FIG. 19, the magnetic field obtained by the forward analysis is drastically misaligned from the value of the magnetic field obtained by the magnetic field sensors when a search path of the hypothetical coil position according to the trust region method once becomes closer to the magnetic field sensors than the position of the actual coil, and as shown in FIG. 20, the function f has a local minimum that is not a global minimum. It should be noted that the trust region method is known to have a tendency to come closer to the true value through a path as shown in FIG. 19 by its nature.

FIG. 20 shows the value of f plotted by 1 [mm] in each axial direction when three points expressed by Formula 21 are sequentially moved in a linear manner. As the actual coil is present between a second point and a third point, the value of f takes zero at a position corresponding to this position. The arrangement of the sensors is the same as in the case in which the number of the sensors is 4 in Simulation 1.

$$\begin{pmatrix} x \\ y \\ z \end{pmatrix} = \begin{pmatrix} 0.70 \\ 0.75 \\ 1.25 \end{pmatrix}, \begin{pmatrix} 0.85 \\ 0.90 \\ 1.10 \end{pmatrix}, \begin{pmatrix} 1.00 \\ 1.05 \\ 1.25 \end{pmatrix}$$ [Formula 21]

As an improvement in order not to take the local minimum (that is not the global minimum) as described above, providing the magnetic field sensors at positions that are sufficiently distant from each other can be conceivable. However, in this embodiment, the positions for the magnetic field sensors to be attached are restricted, and it is difficult in practice to provide the sensors at the positions that are sufficiently distant from each other. Further, it is also conceivable that a disadvantageous effect of being susceptible to disturbance may possibly occur when the magnetic field sensors are too distant from each other.

[Introduction of Random Walk Search Method]

In the transcranial magnetic stimulation treatment, if the position of the coil is misaligned from the optimum position by no smaller than about 5 [mm], for example, there is often a case in which an effect of the treatment is degraded. In such a case, it is necessary to make the error from the true value to be within 5 [mm]. However, as described above, the convergence to the local minimum generally makes it difficult to satisfy this need only based on the trust region method. This is also shown by the result of the simulation described above.

As an algorithm for converging to the global minimum instead of the local minimum, a so-called Simulated Annealing method is known. However, in general, this method is also known to have a difficulty in a practical use such as in setting parameters.

Therefore, an introduction of the random walk search method (RW method) that is relatively easy to be put into practice is considered. Specifically, an algorithm in which the RW method is used from a position at which the update according to the trust region method ends (that is, a position within a range on the order of a few [cm] from the true value) is considered.

In Simulation 2, the convergence property was examined for each of the patterns shown in Table 1 in Simulation 1 using this algorithm. It should be noted that parameters in the RW method are set as listed below.

An upper threshold of the number of times of radius search n: $n_{th}=10$
A lower threshold of the search radius r: $r_{th}=0.1$ [mm]
A radius updating parameter: $\alpha=0.9$
An initial value of the search radius r: $r_0=10$ [mm]

[Result of and Discussion for Simulation 2]

Figure 21:
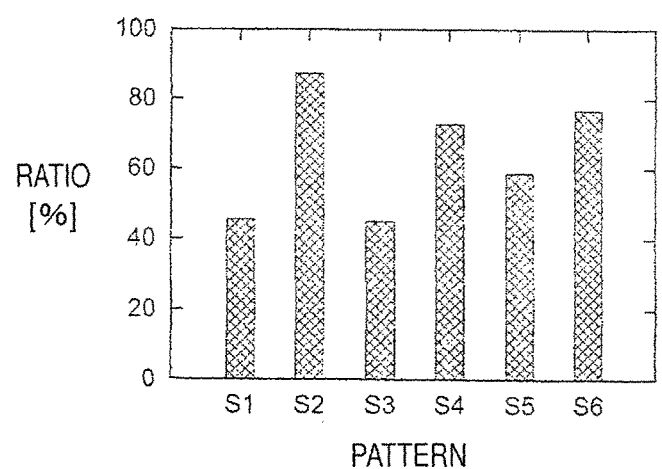
FIG. 21 is a graphical chart showing ratios of the number of trials whose error from a true value is within 1 [mm] in Simulation 2.

FIG. 21 shows a ratio of the number of trials whose error from the true value is within 1 [mm] out of 100 trials for each pattern. As can be clearly seen from FIG. 21, similarly to Simulation 1, the convergence property is clearly better when the hypothetical coil initial position is started from a position closer to the true value (the patterns S2, S4, and S6) than when the hypothetical coil initial position is started from a position distant from the true value (the patterns 51, S3, and S5). Further, in the patterns S2, S4, and S6 in which the hypothetical coil initial position is started from the position closer to the true value, a convergence rate is over 70% regardless of the number of sensors.

Therefore, by combining the trust region method and the RW method, it is possible to estimate the position of the single coil when the posture of the coil is not considered by performing calculation two or three times.

Further, in this treatment, normally, the patient knows the optimum position for himself to some extent, and does not make a mistake about the initial position at which the stimulation coil is placed to a large extent. Therefore, the inverse analysis for a magnetic field can be performed basically only with the random walk method without any problem, and the trust region method can be used only in the case in which the patient makes a mistake about the initial position at which the stimulation coil is placed to a large extent. As the trust region method involves second order partial differential calculation, a burden in the number of calculation increases. Therefore, it can be said that it is preferable not to use the trust region method at all in this viewpoint.

<Simulation 3>

In Simulation 3, a simulation in which the figure-eight spiral coil according to this embodiment is used as the stimulation coil instead of the single coil, and in which the posture of the coil is considered.

As described above, when the patient moves the stimulation coil, it is considered that the position is not misaligned from the optimum position instructed by a specialist in the initial treatment to a large extent (that is, involving a certain degree or more of reproducible nature), a space in which the hypothetical coil initial position occurs can be set near the optimum position. Therefore, in Simulation 3 , the trust region method was not used, and only the RW method was used. It should be noted that X, Y, and Z axes were set as the absolute coordinate system, and U, V, and W axes were set as the coil coordinate system. Further, the arrangement of the sensors is the same as the case in which the number of the sensors is 4 in Simulation 1.

[Execution Procedure]

Figure 22:
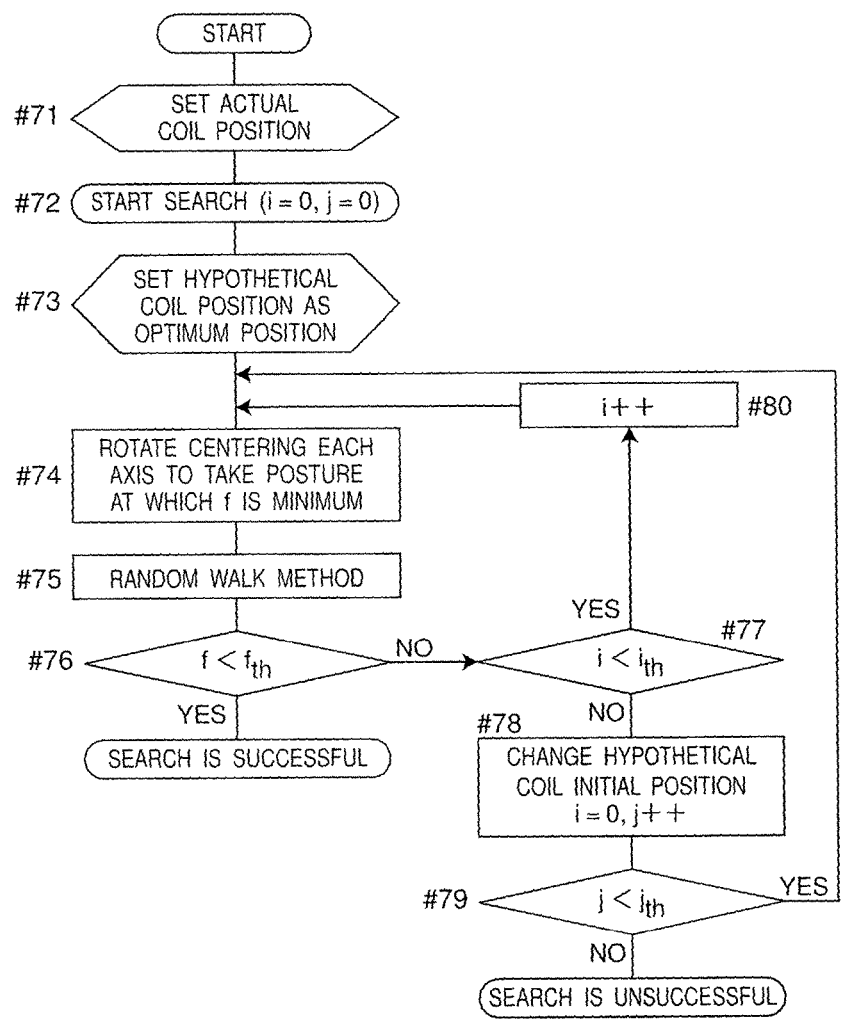
FIG. 22 is a flowchart explaining an execution procedure of Simulation 3.

Next, an execution procedure of Simulation 3 is described with reference to a flowchart of FIG. 22.

Upon starting the simulation, first, in step #71, the actual coil position is set. In Simulation 3 , it was assumed that the patient places the coil at a position slightly misaligned from the optimum position instructed in the initial treatment, and in a posture slightly misaligned from the optimum posture instructed in the initial treatment. Specifically, the actual coil position was set at a position parallelly translated from the optimum position by an initial deviation $s_0$ [cm], and then a posture rotated randomly within a range of β [deg] centering each of the U axis, the V axis, and the W axis was assumed to be the actual coil posture.

Then, in step #72, the search is started. In the initial search state, the number of times of search i=0, and the number of times of update of the hypothetical coil initial position j=0. Upon starting of the search in this initial state, first, the hypothetical coil position is set to be the optimum position (step #73), and the coil posture is rotated centering each of the U axis, the V axis, and the W axis (coordinate conversion) to be a posture where the value of f is minimized (step #74). Subsequently, the RW method is applied (step #75), and it is determined whether or not the calculated value of f at the hypothetical current coil position is smaller than an upper threshold $f_{th}$ ($f<f_{th}$) (step #76). If the determination result in step #76 is YES, the search is successful.

By contrast, if the determination result in step #76 is NO, in step #77, it is determined whether or not the number of times of search i does not reach an upper threshold $i_{th}$ ($i<i_{th}$). If the number of times does not reach the upper threshold (step #77: YES), in step #80, a counting number of the number of times of search i is incremented (that is, the counting number increases only by 1), and the process returns to step #74 and the steps of step #74 and after are repeated. Alternatively, if the determination result in step #77 is NO, the number of times of search i has reached the upper threshold $i_{th}$. Therefore, in step #78, the hypothetical coil initial position is changed.

In step #78, the hypothetical coil initial position is set to be different from the optimum position by $s_1=5.0\gamma$ [cm] (a random constant number within a range of $\gamma$: $0<\gamma<1$), for example, the counting number of the number of times of search reset (i=0), and a counting number of the number of times of update j of the hypothetical coil initial position is incremented (that is, the counting number j increases only by 1). Then, further, in step #79, it is determined whether or not the number of times of update j of the hypothetical coil initial position does not reach the upper threshold $j_{th}$ ($j<j_{th}$). If the determination result in step #79 is YES, the process returns to step #74 and the steps of step #74 and after are repeated. By contrast, if the determination result in step #79 is NO, the search is unsuccessful as the number of times of update j of the hypothetical coil initial position has reached the upper threshold $j_{th}$, and the search is terminated.

[Evaluation of Optimum Position (Determination of $f_{th}$)]

The above simulation was carried out while knowing the actual coil position, and therefore it was possible to determine whether or not the convergence was made could be determined by comparing the position and posture of the coil when the search has ended with the actual coil position and posture. However, in order to perform the treatment in practice, the actual coil position (a position at which the patient placed the coil) is unknown, and it is necessary to determine whether or not the convergence is made based only on the f value according to the least-square approach. Therefore, it is necessary to examine how many the value of f should be decreased to satisfy requested specifications, in other words, how many the threshold value $f_{th}$ in the algorithm described with reference to FIG. 22 should be set.

Here, the requested specifications are calculated preferably based on a clinical research. In this embodiment, it is set that the errors of the center position and posture of the coil are within ranges listed below, for example.

Figure 23A:
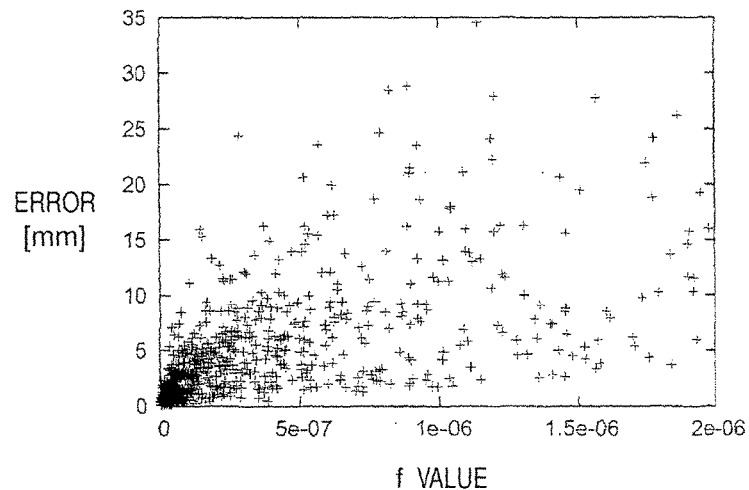
FIG. 23A is a graphical chart showing correlation between a function f of a least-square approach and an error of the coil position.
Figure 23B:
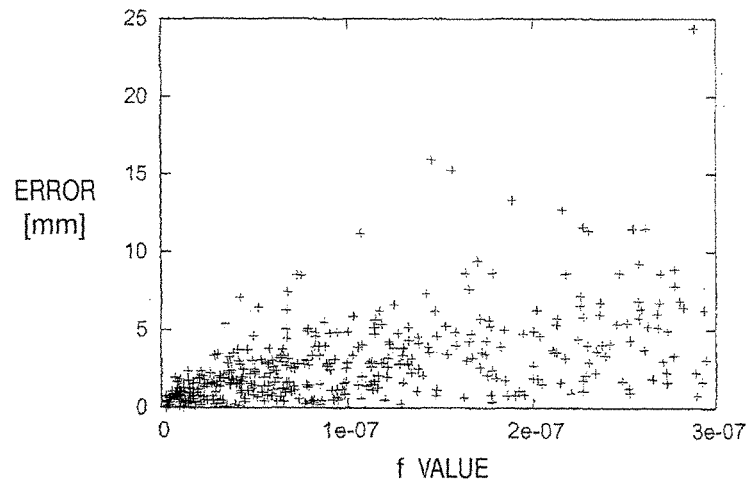
FIG. 23B is a graphical chart enlarging a part of FIG. 23A.
Figure 24A:
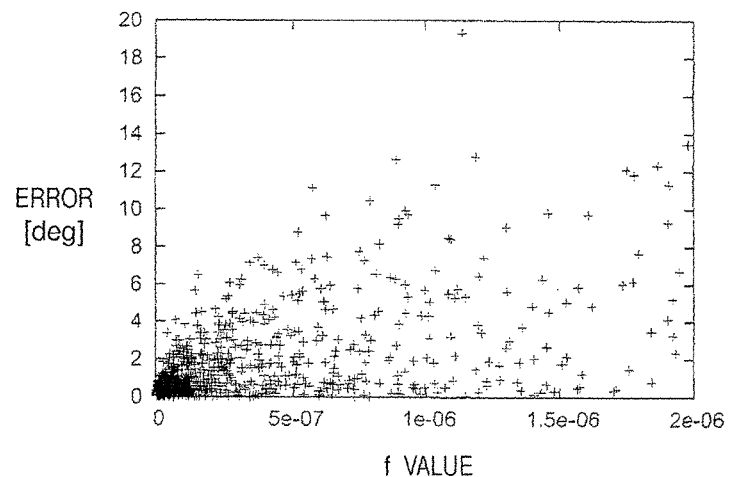
FIG. 24A is a graphical chart showing correlation between the function f and a roll angle error of the coil.
Figure 24B:
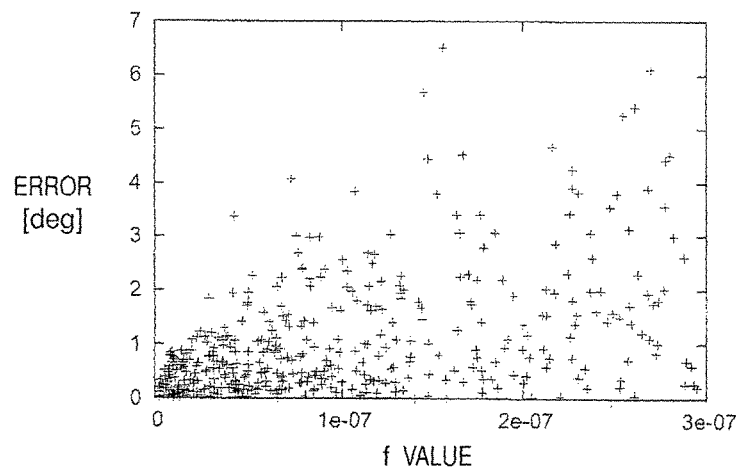
FIG. 24B is a graphical chart enlarging a part of FIG. 24A.
Figure 25A:
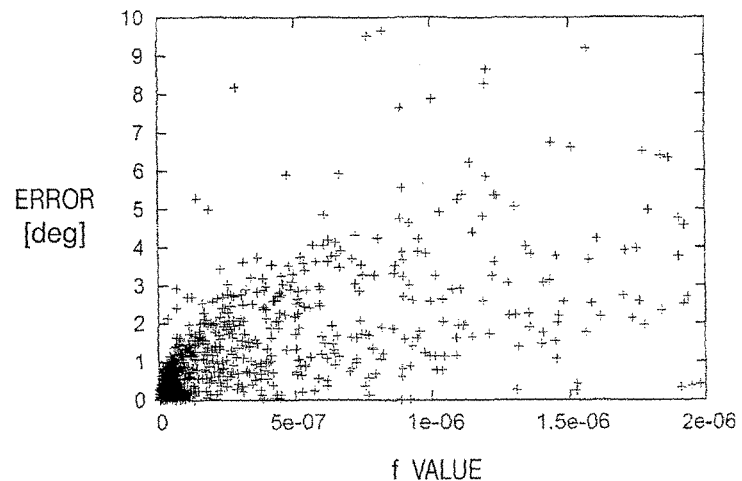
FIG. 25A is a graphical chart showing correlation between the function f and a pitch angle error of the coil.
Figure 25B:
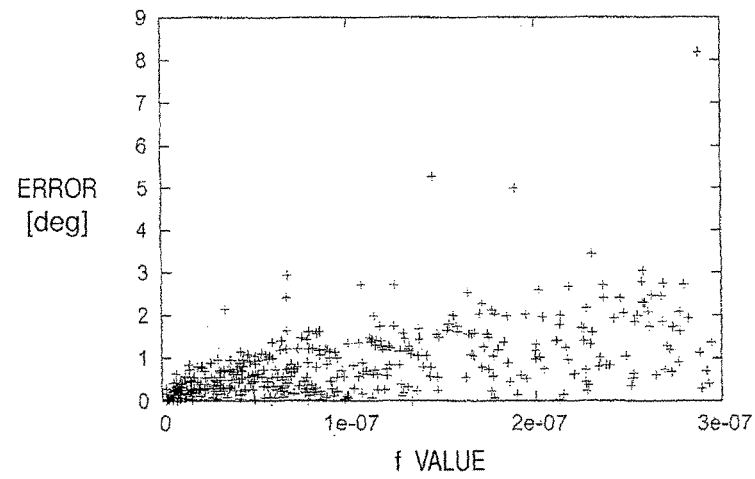
FIG. 25B is a graphical chart enlarging a part of FIG. 25A.
Figure 26A:
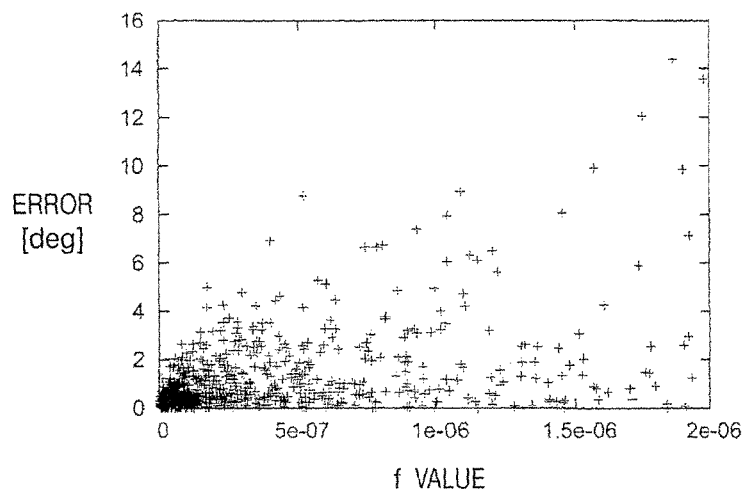
FIG. 26A is a graphical chart showing correlation between the function f and a yaw angle error of the coil.
Figure 26B:
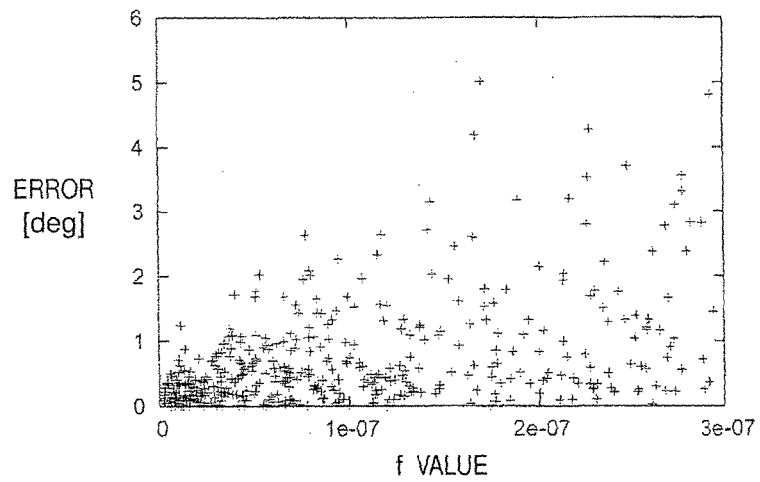
FIG. 26B is a graphical chart enlarging a part of FIG. 26A.

The error of the center position of the coil: within 5 [mm]
The error of the posture of the coil: within 5 [deg] with respect to each axis of the coil FIG. 23A is a correlation chart showing correlation between the value of f based on the least-square approach and the error from the optimum position, and FIG. 23B is a chart enlarging a part of FIG. 23A. Further, FIGS. 24A and 24B are correlation charts showing correlation between the value of f and a roll angle error, FIGS. 25A and 25B are correlation charts showing correlation between the value of f and a pitch angle error, and FIGS. 26A and 26B are correlation charts showing correlation between the value of f and a yaw angle error. Here, the roll angle refers to a rotational angle centering the U axis shown in FIG. 14 and FIG. 15, and the pitch angle and the yaw angle respectively refer to rotational angles centering the V axis and the W axis.

As shown in FIGS. 23A and 23B to FIGS. 26A and 26B, it was found that all of these errors increase when the value of f based on the least-square approach increases, and the value of f and each of the errors have a positive correlation.

Further, from FIGS. 23A and 23B, a condition that the error of the value of f based on the least-square approach from the optimum position satisfies the requested specification is generally $f<5.0\times10^{-8}$. Moreover, from FIGS. 24A and 24B to FIGS. 26A and 26B, a condition that the error of the value of f from the optimum posture satisfies the requested specification is generally $f<1.5\times10^{-7}$. Therefore, by setting $f_{th}=5.0\times10^{-8}$, it is possible to determine the coil position almost correctly.

[Reliability of Determined Position and Posture of Coil]

The smaller the value of $f_{th}$ is set, the more improved the reliability of the determined position and posture of the coil is. By contrast, an average time length required for the inverse analysis increases in general. In a practical aspect, it is important to intend to reduce the time length required for an analyzing process while ensuring reliability required according to situations.

The transcranial magnetic stimulation treatment is performed while the stimulation coil is pressed against the head of the patient. Therefore, a tolerance for the error in a direction of the W axis in the coil coordinate system (a direction perpendicular to the coil plane: see FIG. 14) is relatively large, and it is considered that the threshold value for the error of the position can be slightly increased. Further, it can be seen from FIGS. 23A and 23B to FIGS. 26A and 26B that it is highly probably that the requested specifications are satisfied even where $f_{th} \geq 5.0\times10^{-8}$. Therefore, regardless of the situation, it is inadvisable to exclude an entire range of $f_{th} \geq 5.0\times10^{-8}$.

For example, in such a case in which the current position of the coil is largely distant from the optimum position, it is generally considered to be better to prioritize to recognize the overall position and posture of the coil in a shorter period of time even if the reliability slightly reduces so as to move the coil closer to the optimum position as quickly as possible, rather than taking time to improve the reliability of the coil position.

Therefore, it is possible to define a relation between the value of f based on the least-square approach and the reliability as shown in Table 3 shown below, for example, and the patient is informed of information of the position and posture of the coil obtained by the inverse analysis together with reliability of the information. In the transcranial magnetic stimulation treatment, when the stimulation is applied to a position that is somewhat misaligned from the optimum position, in general, there is no problem in the safety while the effect of the treatment is reduced. For example, it is possible to for the patient to select the information according to the reliability such that if the patient feels the effect of the treatment is small in the treatment based on the information with poor reliability, the information with poor reliability is not used in the treatment.

TABLE 3

| Value of f | Achievement rate of requested specifications (%) | Reliability |
| --- | --- | --- |
| Smaller than $5.0 \times 10^{-8}$ | 99 | S |
| Smaller than $2.0 \times 10^{-7}$ | 87 | A |
| Smaller than $3.0 \times 10^{-7}$ | 78 | B |
| Not smaller than $3.0 \times 10^{-7}$ | Unknown | E |

[Determination of the Initial Value of f ($f_0$)]

In the examination of the inverse analysis for a magnetic field as described above, it was found that there is a tendency, if the value of f when starting the search (initial value ($f_0$)) is above a certain level, the requested specifications are almost unfailingly not satisfied (that is, the search is unsuccessful). In such a case, if the initial value of f ($f_0$) is greater than the threshold value, it is possible to reduce a time length for analysis by setting such that the search from this position is not performed from the start (so-called filtered).

Figure 27:
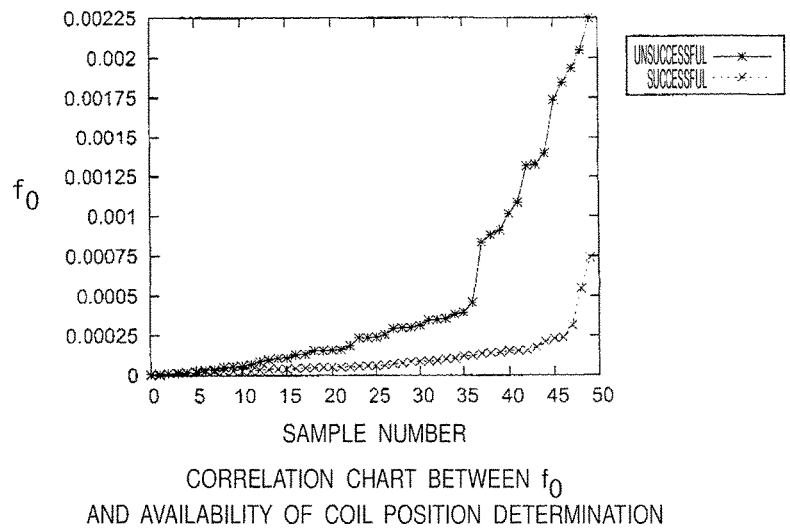
FIG. 27 is a graphical chart showing correlation between an initial value of $f(f_0)$ when starting the search and whether or not the coil position can be determined.

FIG. 27 shows correlation between the initial value of f ($f_0$) when starting the search and whether or not the coil position can be determined. In the graphical chart shown in FIG. 27, 50 pieces of data for $f_0$ when the requested specifications were not satisfied and 50 pieces of data for $f_0$ when the requested specifications were satisfied after the search performed based on the RW method are plotted. From the graphical chart of FIG. 27, it is found that about a half of trials in which the search is unsuccessful are omitted by using a filter of the search is not performed when $f_0 > 2.5 \times 10^{-4}$, while trials in which the search is successful are rarely omitted, and it is possible to improve efficiency of the search.

[Searchable Range and Convergence Time]

Considering $f_{th}$ and $f_0$ as described above, an extent to which the inverse analysis is possible is examined. Specifically, an extent of the misalignment to which the determination of the position of the coil is possible in a case in which the patient places the stimulation coil from a position misaligned from the optimum position is examined.

In this examination, initial conditions are set as shown in Table 4. For each pattern shown in Table 4, 100 search trials are performed with changing the optimum position and posture. Explaining taking a pattern $T_{12}$ in Table 4 as an example, in the pattern $T_{12}$, the patient places the coil at a position misaligned from the optimum position by 1 [cm], the posture of the coil is rotated 100 times randomly within a range of ±20 [deg] centering each axis, and then the search trials are performed. In the remaining patterns, the same method is employed other than the range of combinations of an error $s_0$ and an error β. It should be noted that the examination was conducted by setting an upper threshold ($i_{th}$) of the number of times of execution of the RW method to be 1000, and setting an upper threshold ($j_{th}$) of the number of times of update of the search initial position to be 10.

TABLE 4

| Pattern | Error $S_0$ from optimum position (cm) | Error β from optimum posture (deg) |
| --- | --- | --- |
| $T_{10}$ | 1 | ±0 |
| $T_{11}$ | 1 | ±10 |
| $T_{12}$ | 1 | ±20 |
| $T_{13}$ | 1 | ±30 |
| $T_{30}$ | 3 | ±0 |

TABLE 4-continued

| Pattern | Error $S_0$ from optimum position (cm) | Error β from optimum posture (deg) |
| --- | --- | --- |
| $T_{31}$ | 3 | ±10 |
| $T_{32}$ | 3 | ±20 |
| $T_{33}$ | 3 | ±30 |
| $T_{50}$ | 5 | ±0 |
| $T_{51}$ | 5 | ±10 |
| $T_{52}$ | 5 | ±20 |
| $T_{53}$ | 5 | ±30 |

FIG. 28 to FIG. 31 are graphical charts showing ratios of convergence when performing the trials with changing the optimum position and posture 100 times for respective patterns.

Figure 28:
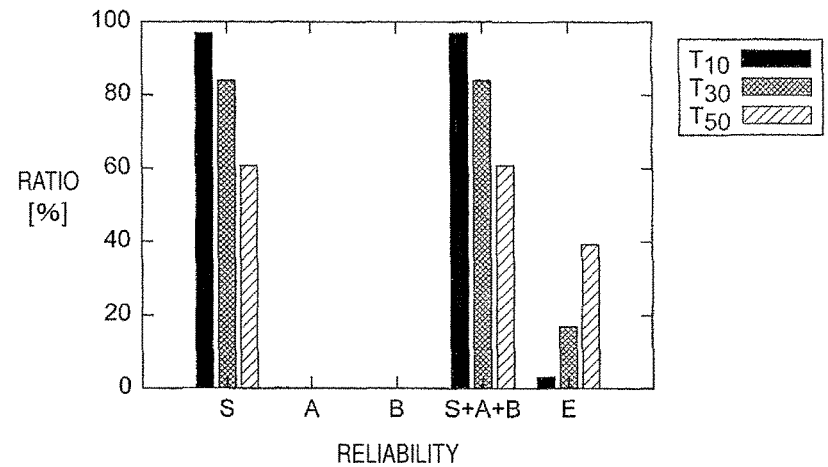
FIG. 28 is a graphical chart showing ratios of convergence for a pattern in which an error from an optimum posture is zero.
Figure 29:
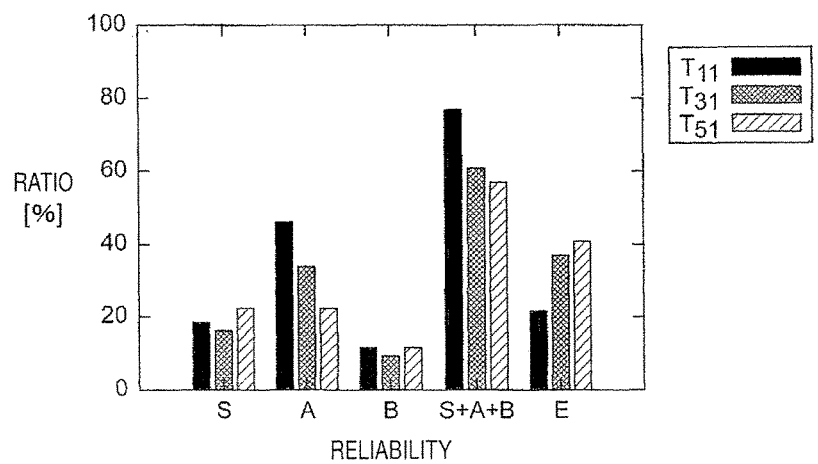
FIG. 29 is a graphical chart showing ratios of convergence for a pattern in which the error from the optimum posture is random within a range of ±10 [deg].
Figure 30:
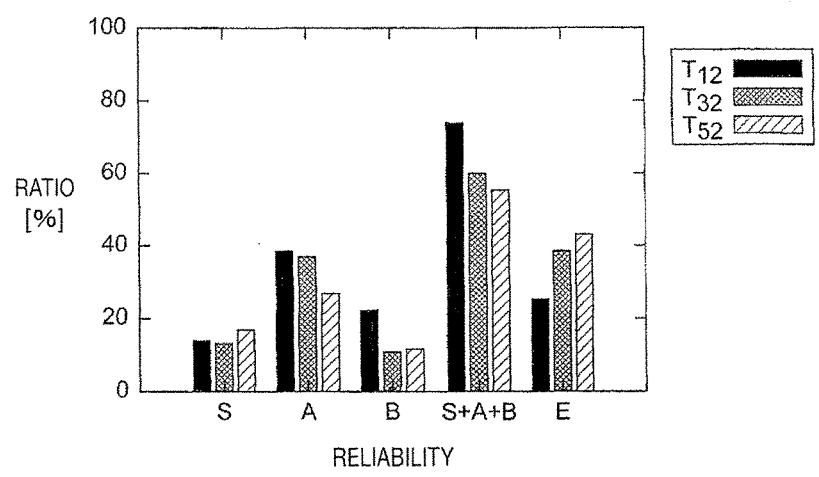
FIG. 30 is a graphical chart showing ratios of convergence for a pattern in which the error from the optimum posture is random within a range of ±20 [deg].
Figure 31:
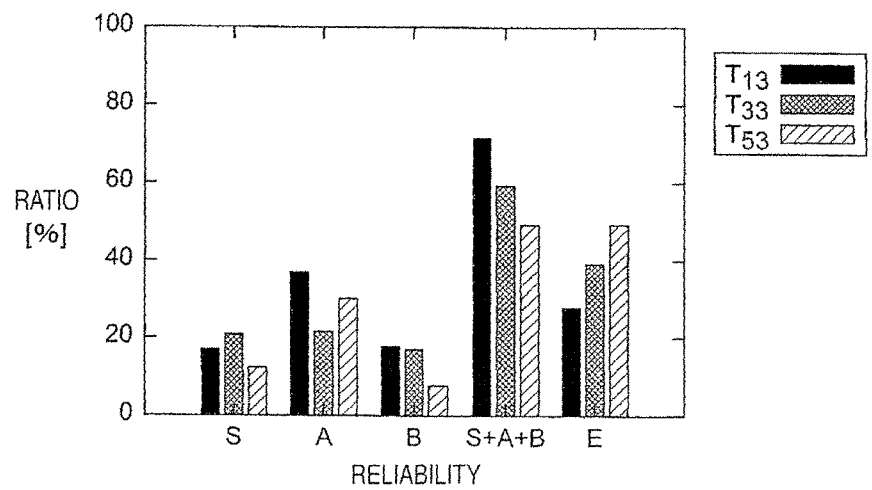
FIG. 31 is a graphical chart showing ratios of convergence for a pattern in which the error from the optimum posture is random within a range of ±30 [deg].

Describing more specifically, FIG. 28 shows the ratios of convergence for a combination of the three patterns ($T_{10}$, $T_{30}$, $T_{50}$) in which the error β from the optimum posture is zero (β=±0 [deg]), FIG. 29 shows the ratios of convergence for a combination of the three patterns ($T_{11}$, $T_{31}$, $T_{51}$) in which the error β from the optimum posture is random within a range of ±10 [deg] and the error $s_0$ from the optimum position is different for each pattern, FIG. 30 shows the ratios of convergence for a combination of the three patterns ($T_{12}$, $T_{32}$, $T_{52}$) in which the error β from the optimum posture is random within a range of ±20 [deg] and the error $s_0$ from the optimum position is different for each pattern, and FIG. 31 shows the ratios of convergence for a combination of the three patterns ($T_{13}$, $T_{33}$, $T_{53}$) in which the error β from the optimum posture is random within a range of ±30 [deg] and the error $s_0$ from the optimum position is different for each pattern. It should be noted that, in each chart, reliability E shows a ratio in which the reliability was not improved above reliability B even if the search was performed with changing the initial position of the search 10 times.

From FIG. 28, it can be seen that it is possible to determine the position of the coil at extremely high reliability when the error β from the optimum posture is zero (β=±0 [deg]). Further, from FIG. 28 to FIG. 31, it can be seen that the ratio of successful determination of the position and posture of the coil decreases as it becomes more distant from the optimum position of the coil. Regarding the initial posture, although the pattern similar to the optimum posture has a slightly higher convergence rate, its advantage is not very distinctive. In other words, it is found that the error ($s_0$) of the coil position has a greater influence on the inverse analysis of the coil than the error (β) of the coil posture.

As a ratio in which the reliability is improved above the reliability B (S+A+B) is about 50% in the pattern $T_{53}$ (see FIG. 31), it is expected that the ratio further decreases below 50% if the error $s_0$ from the optimum position exceeds 5 [cm]. The more the convergence rate deteriorates, the longer it takes to perform the inverse analysis, and the more stress is given to the patient. Therefore, in order to allow the patient to guide the coil smoothly, it is preferable that the error $s_0$ from the optimum position be within 5 [cm].

Further, it is not very conceivable that the patient moves the coil very quickly. Therefore, it is supposed that once the position of the coil is determined, then the patient sets the initial position of the hypothetical coil at a position near the coil position. Specifically, it is possible to perform the inverse analysis always from the position near the actual coil position, and to recognize the position of the coil at high reliability.

Table 5 shows convergence time when $f_{th}<3.0\times10^{-7}$ is satisfied and the position of the coil is determined for each pattern shown in Table 4.

TABLE 5

| Pattern | Average search time (sec) | Shortest search time (sec) | Longest search time (sec) | Convergence rate (%) |
|---|---|---|---|---|
| $T_{10}$ | 0.63 | 0.51 | 0.78 | 97 |
| $T_{11}$ | 1.65 | 0.60 | 7.15 | 78 |
| $T_{12}$ | 1.62 | 0.63 | 7.79 | 74 |
| $T_{13}$ | 1.75 | 0.55 | 8.22 | 72 |
| $T_{30}$ | 0.67 | 0.59 | 0.77 | 84 |
| $T_{31}$ | 1.69 | 0.71 | 6.87 | 62 |
| $T_{32}$ | 1.50 | 0.69 | 7.12 | 61 |
| $T_{33}$ | 1.49 | 0.66 | 8.90 | 60 |
| $T_{50}$ | 0.71 | 0.54 | 0.92 | 61 |
| $T_{51}$ | 1.47 | 0.74 | 6.54 | 58 |
| $T_{52}$ | 1.26 | 0.71 | 8.09 | 56 |
| $T_{53}$ | 1.40 | 0.75 | 5.05 | 50 |

As shown in Table 5, the search time takes a minimum of 0.51 [sec] and a maximum of 8.90 [sec]. In this simulation, when the position is not converged in a single search trial, the initial position of the hypothetical coil for search is changed up to 10 times and the search is performed. Therefore, if the initial position is changed many times, it takes more time for the search by the number of times of change. Further, comparing the average search time, the position is converged within 1 [sec] in the case of the patterns $T_{10}$, $T_{30}$, and $T_{50}$, and about 1.5 [sec] in the case of the remaining patterns. From these results, although the convergence rate decreases as the initial position of the hypothetical coil is more distant from the optimum position, the time required for convergence in any of the patterns is nearly the same when converging.

As described above, according to this embodiment, by using the above method, it is possible to perform the inverse analysis to the magnetic field generated by the stimulation coil 11 based on the detection signals from the plurality of magnetic field sensors 13, and to determine the current position and posture of the stimulation coil 11. In particular, by employing the random walk search method, it is possible to relatively easily converge the function f in the least-square approach to the global minimum instead of the local minimum. Therefore, it is possible to determine the current position and posture of the stimulation coil 11 more reliably.

Realizing the above described inverse analysis for a magnetic field contributes to downsizing, cost reduction, and facilitation of handling of the magnetic stimulator 10. This, in turn, allows the patient M to perform the transcranial magnetic stimulation treatment at home or at the personal doctor s office in the neighborhood continuously and repeatedly on a daily basis.

In the above description, utilizing the inverse analysis method using the information relating to intensity and direction of the magnetic field detected by a magnetic field detecting means (the magnetic field sensor 13), the stimulation coil is guided to the three-dimensional position and posture corresponding to the optimum position and posture at which the magnetic stimulation is to be applied. However, instead of or in addition to this, it is possible to guide the stimulation coil to the three-dimensional position (and posture) corresponding to the optimum position (and posture) by utilizing a set of pieces of data combining the information (data) of at least the position (more preferably, the position and posture) of the magnetic field generating means, and the information (data) relating to the intensity and direction of the magnetic field generated at said position and detected by the magnetic field detecting means (in the specification, the combination of the data is referred to as a data set).

An embodiment based on a method using this data set (hereinafter referred to as a second embodiment, as needed) is now described. In the description below, as to the components having basically like or similar configuration and having basically like or similar functions as in the embodiment utilizing the inverse analysis method (hereinafter referred to as the first embodiment, as needed), they are denoted by like or similar reference numerals, and explanations for these components are omitted.

Figure 32:
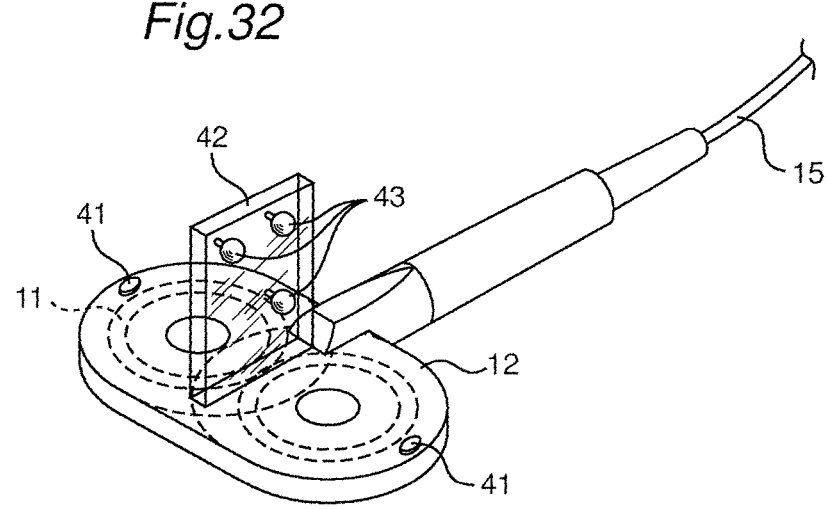
FIG. 32 is a perspective view illustrating one example of a stimulation coil and a coil holder used in an experiment of an embodiment (second embodiment) according to a method using a data set.

FIG. 32 is a perspective view illustrating one example of the stimulation coil and the coil holder used in an experimental example in this embodiment. As shown in this figure, the stimulation coil 11 used in the experimental example of the second embodiment is a so-called figure-eight spiral coil that is used in the first embodiment, and more preferably, resin-molded monolithically with the coil holder 12 when molding the coil holder 12 made of synthetic resin. It should be appreciated that, similarly to the first embodiment, examples of the stimulation coil to be used include various types of known magnetic coils.

In this embodiment, at predetermined portions of the coil holder 12, permanent magnets 41, 41 as a static magnetic field generating means for detecting a position are respectively fixed to surface portions that are further outward from both ends of the stimulation coil 11 in a longitudinal direction, for example.

Further, a transparent plate-like base plate 42 made of resin, for example, is uprightly fixed on an upper surface of the coil holder 12, in a direction perpendicular to the longitudinal direction of the stimulation coil 11 and at a center portion of the stimulation coil 11 in a longitudinal direction. It is preferable that the base plate 42 be fixed to the coil holder 12 using a screw member, for example, in a detachable manner.

Further, the base plate 42 is provided with a so-called Polaris marker 43, which is used as a detection target marker when a position of the coil holder 12 (that is, the position of the stimulation coil 11) using a known optical tracking system (POLARIS manufactured by NDI, for example). The number of the marker 43 provided is preferably more than one. In this case, it is more preferable that the three spherical markers 43 be positioned respectively at apices of a triangle of a predetermined shape on the base plate 42.

In the example shown in FIG. 32, a static magnetic field generating means (permanent magnets 41, 41) is used in order to detect the position of the coil holder 12 (that is, the position of the stimulation coil 11). In this case, by detecting static magnetic fields generated by the permanent magnets when generation of the dynamic magnetic field by the stimulation coil 11 is stopped, it is possible to avoid the interference of the dynamic magnetic field, and to accurately detect positioning signals by the static magnetic fields generated by the permanent magnets. However, it is also possible to detect the static magnetic fields (permanent magnets) in the treatment without stopping the generation of the dynamic magnetic field and to detect the position of the coil holder 12, by providing the plurality of magnetic field sensors having different sensitivities to each other.

In addition, alternatively, as described in the description of the first embodiment, the position detection can be performed using the dynamic magnetic field generating means (the stimulation coil 11, for example).

Figure 33:
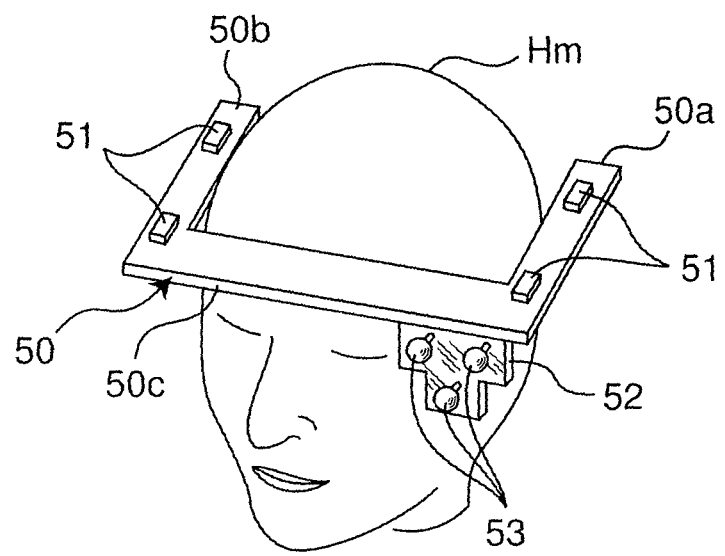
FIG. 33 is a perspective view illustrating one example of a magnetic sensor fixation member used in the experiment of the second embodiment.

FIG. 33 is a perspective view illustrating one example of a magnetic field sensor fixation member for fixing the magnetic field sensors at a predetermined relative position with respect to the particular portion of the patient. A magnetic field sensor fixation member 50 is configured as a frame body in a square U shape in a planar view, and the dimensions and the shape of the frame body 50 are set such that its inner edge portion is fixedly engaged to the patient s head. It should be noted that in the experimental example of this embodiment, a head Hm of a dummy is used in place of the patient s head.

Preferably a plurality of magnetic field sensors 51 are fixed to an upper surface of the frame body 50. In this experimental example, the number of the magnetic field sensors 51 that are used is four in total, and a back and forth pair of magnetic field sensors 51 are attached to either of left and right side portions 50a and 50b of the frame body 50. With this, it is possible to detect the magnetic field at four positions back and forth, and left and right that surround the head Hm (that is, to detect the intensity and direction of the magnetic field). As the magnetic field sensors 51, preferably, so-called triaxial sensors are used. It is appreciated that, similarly to the first embodiment, various types of known magnetic field sensors can be used alternatively.

It should be noted that, in this experimental example, it is more preferable that the base plate 52 made of resin, for example, is fixed drooping downward at a predetermined portion of a front side 50c of the frame body 50. The base plate 52 is provided with three spherical Polaris markers 53 as detection targets to be detected by the optical tracking system. The markers 53 are used for evaluation of the errors in the experiment.

The magnetic field sensor fixation member 50 serves as the fixing means configured to fix the positions of the plurality of magnetic field sensors 13 (four, for example, in this embodiment) with respect to the patients head. Similarly to the first embodiment, the positions at which the magnetic field sensors 13 are to be fixed on the patient s head is required to be reproducible, and it is necessary to fix the magnetic field sensors 13 always at the same positions of the patient. It is desirable to use a familiar appliance (body fitment) that can be frequently worn on a daily basis as a means for fixing the magnetic field sensors 13 on the patient s head in a relatively natural manner without giving a uncomfortable or unpleasant feeling to the patient while ensuring repeatability and reproducibility of the positions to be fixed.

Therefore, similarly to the first embodiment, it is preferable that body fixings such as a pair of eyeglasses, in particular, a pair of protective (safety) glasses and goggles for sporting, a pair of earpieces, a pair of headphones, and a headband be used in practice.

In the example shown in FIG. 33, the four magnetic field sensors 13 are attached to the magnetic field sensor fixation member 50, but the number of the magnetic field sensors to be used can be other than four. As has been widely known, while using more sensors is generally preferable in order to improve measurement accuracy, this also makes the system complicated and increases the costs. Accordingly, it is desired to use the smaller number of sensors as much as possible. Even in this case, it is preferable to use at least two sensors in order to ensure a certain degree of measurement accuracy, and it is more preferable to provide the sensors isotropically with respect to the patient s head.

Describing more specifically using the coil holder 12 and the magnetic field sensor fixation member 50, as described above, in this embodiment, the coil holder 12 that holds the stimulation coil 11 is provided with the permanent magnets 41, for example, the magnetic field sensor fixation member 50 is attached to the patient in the hospital. And, the magnetic field data (data relating to the intensity and direction of the magnetic fields) obtained by detecting the magnetic fields generated by the permanent magnets 41 of the coil holder 12 by the magnetic field sensors 13 and the data of the three-dimensional position and posture of the coil holder 12 (that is, of the stimulation coil 11) obtained by such as an optical tracking system are measured at the same time, and a combination of the both data is recorded as a single data set. Then, the data set is collected and recorded for each of the optimum stimulating position determined by the doctor according to the conventional method and a plurality of (a large number of) positions around this position.

Examples of the data set thus collected are shown in Table 6.

In these examples, the number of the magnetic sensors is four, respectively represented with subscripts of a, b, c, and d. For the position and posture of the coil, the center position of the coil is represented by P, and the posture of the coil is represented by R. Further, pieces of data that are represented with subscripts of 1-N correspond to data sets 1-N, respectively. As the magnetic sensors respectively measure values in the three directions of x, y, and z, pieces of magnetic field data $B_a$-$B_d$ are three-dimensional vectors and their directions are represented with subscripts of x, y, and z, respectively. For the magnetic sensor represented with the subscript a, the magnetic field data $B_{a1}$ is expressed by a formula below taking the example of the data set 1.

$$B_{a1}=(B_{a1x}, B_{a1y}, B_{a1z})$$

Likewise, the position data P and the posture data R are also three-dimensional vectors, and a position data $P_1$ is expressed by a formula below taking the example of the data set 1.

$$P_1=(P_{1x}, P_{1y}, P_{1z})$$

Further, a posture data R1 is expressed by a formula below taking the example of the data set 1, where the roll angle is α, the pitch angle is β, and the yaw angle is γ.

$$R_1=(\alpha_1, \beta_1, \gamma_1)$$

TABLE 6

| Data set number | Magnetic field | Position and posture of coil |
| --- | --- | --- |
| 1 | ($B_{a1}$, $B_{b1}$, $B_{c1}$, $B_{d1}$) | ($P_1$, $R_1$) |
| 2 | ($B_{a2}$, $B_{b2}$, $B_{c2}$, $B_{d2}$) | ($P_2$, $R_2$) |
| ... | ... | ... |
| N | ($B_{aN}$, $B_{bN}$, $B_{cN}$, $B_{dN}$) | ($P_N$, $R_N$) |

Figure 34:
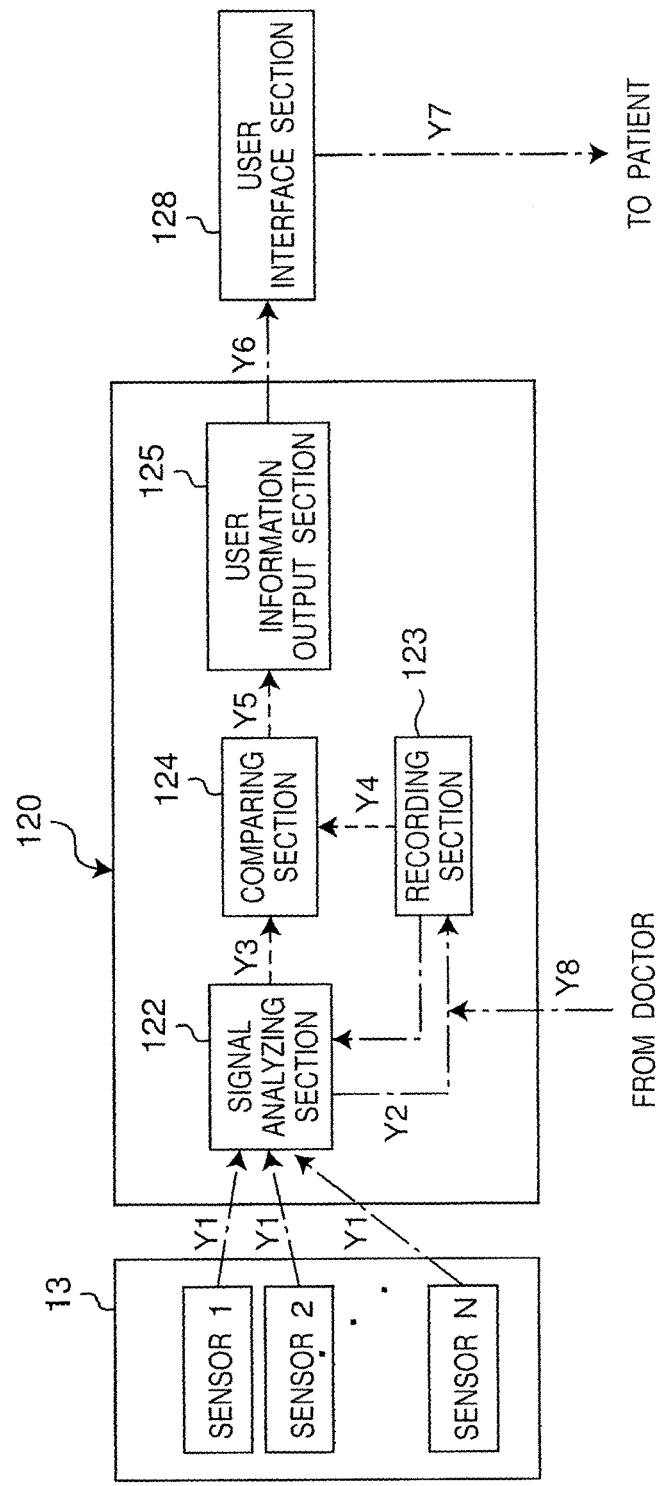
FIG. 34 is a block diagram schematically illustrating a configuration of a data set analyzing unit used in the second embodiment.

FIG. 34 is a block diagram schematically illustrating a configuration of a data set analyzing unit used in the second embodiment.

The data set analyzing unit 120 is configured by a so-called personal computer having a CPU (central processing unit) as a main section, for example, and as shown in a block diagram of FIG. 34, is provided with a signal analyzing section 122, a recording section 123, a comparing section 124, and a user information output section 125.

The signal analyzing section 122 is configured to, based on detection signals inputted from the plurality of the magnetic field sensors 13 (sensor 1, sensor 2, . . . , and sensor N) that are inputted preferably as wireless signals (see an arrow Y1 in FIG. 34), obtain the magnetic field data of the magnetic fields generated by the permanent magnets 41 of the coil holder 12 (data relating to the intensity and direction of the magnetic fields), and inputs the obtained data to the recording section 123 (see an arrow Y2 in FIG. 34). At the same time, the doctor, for example, obtains the data for the three-dimensional position and posture of the coil holder 12 (that is, of the stimulation coil 11) obtained by the optical tracking system, and inputs the obtained data to the recording section 123 (see an arrow Y8 in FIG. 34).

The recording section 123 is configured to record a combination of the magnetic field data and the data of the three-dimensional position and posture thus obtained by the simultaneous measuring as a single data set, and to collect and record data sets for the optimum stimulating position and posture determined by the doctor according to the conventional method and for a plurality of (a large number of) positions and postures around this position and posture. The recording section 123 is configured as a readable memory device.

The comparing section 124 is configured to compare the magnetic field data obtained by the signal analyzing section 122 in the treatment and such with the data sets recorded in the recording section 123 (see arrows Y3 and Y4 in FIG. 34). In this case, one of the recorded data sets whose magnetic field is closest to (if not identical with) the magnetic field in the magnetic field data obtained by the signal analyzing section 122 is extracted. Based on the data of the three-dimensional position and posture in the extracted data set, it is possible to sense the deviation (misalignment) from the data of the three-dimensional position and posture (three-dimensional reference data) corresponding to the optimum stimulating position and posture.

Then, a signal of the data of the three-dimensional position and posture of the data set extracted based on a result of the comparison by the comparing section 124 is outputted to a user interface section 128 (the display device in this embodiment) via the user information output section 125 (see arrows Y5 and Y6 in FIG. 34). At this time, it is preferable that the signal of the three-dimensional data of the optimum stimulating position and posture (three-dimensional reference data) be previously inputted to the user interface section 128 (display device). It should be noted that the magnetic field data corresponding to the three-dimensional reference data is reference magnetic field data.

The user interface section 128 is configured to generate, based on the outputted signal from the user information output section 125, instruction information indicating an operation of displacement to be performed using the operating means (coil holder 12) (in the case of the display device, a signal for displaying such as a video signal), and provides the user with the generated information.

The operator (user) of the coil holder 12 manipulates the coil holder 12 to displace along the scalp of the patient while watching the display device 128 (see an arrow Y7 in FIG. 34) such that the deviation shown in a screen of the display device 128 is close to zero as much as possible. Then, the manipulation of the stimulation coil 11 to displace is stopped at the position and posture of the stimulation coil 11 at which the deviation shown in the screen of the display device 128 is zero or close to zero as much as possible, and this state is maintained. At this time, similarly to the first embodiment, it is convenient to fix the coil holder 12 using the holder fixation member.

Figure 35:
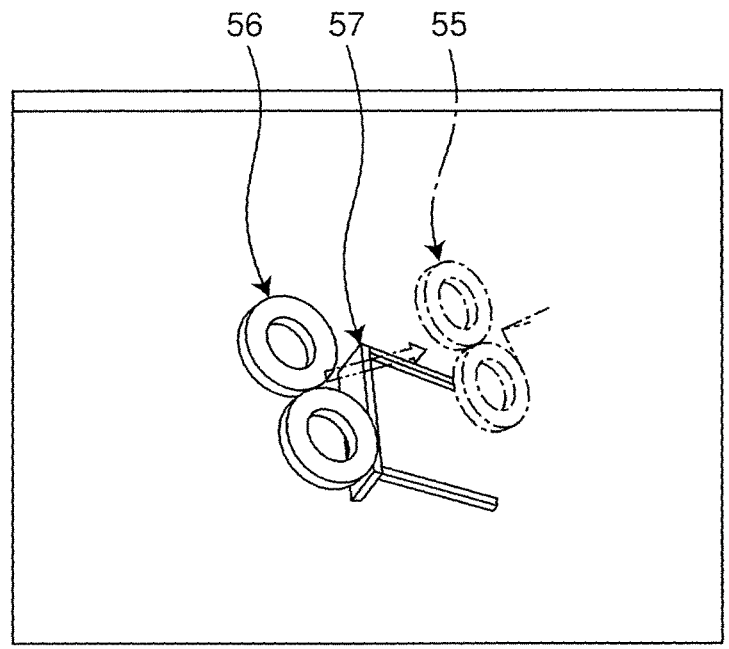
FIG. 35 is an explanatory view illustrating an example of an image displayed in a screen of a display device used in the second embodiment.

In this embodiment, Open GL is installed as a program interface for graphic in order to display an image in the display device 128 so that, as shown in FIG. 35, a coil holder image 55 corresponding to the optimum stimulating position (one-dot chain line in FIG. 35) and a coil holder image 56 at the current position (solid line in FIG. 35) are displayed in the same screen. It should be noted that, more preferably, a sensor fixation member image 57 is displayed in the same screen.

Therefore, the operator (user) of the coil holder 12 is only required to manipulate the coil holder 12 to displace along the scalp of the patient while watching the display device 128 such that the coil holder image 56 in a solid line (current position) displayed in the screen overlaps with the coil holder image 55 in an alternate long and short dash line (optimum stimulating position) as much as possible.

Figure 36:
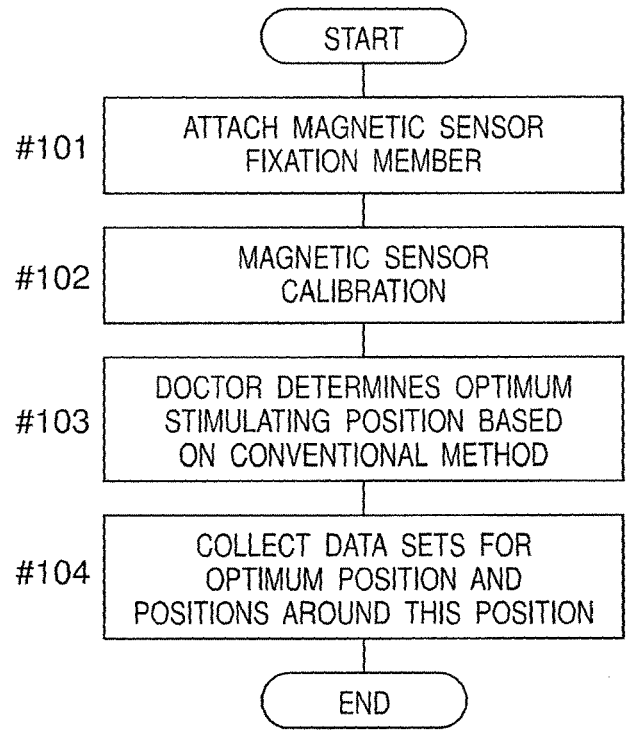
FIG. 36 is a flowchart explaining an operation method of a magnetic stimulator in a hospital according to the second embodiment.
Figure 37:
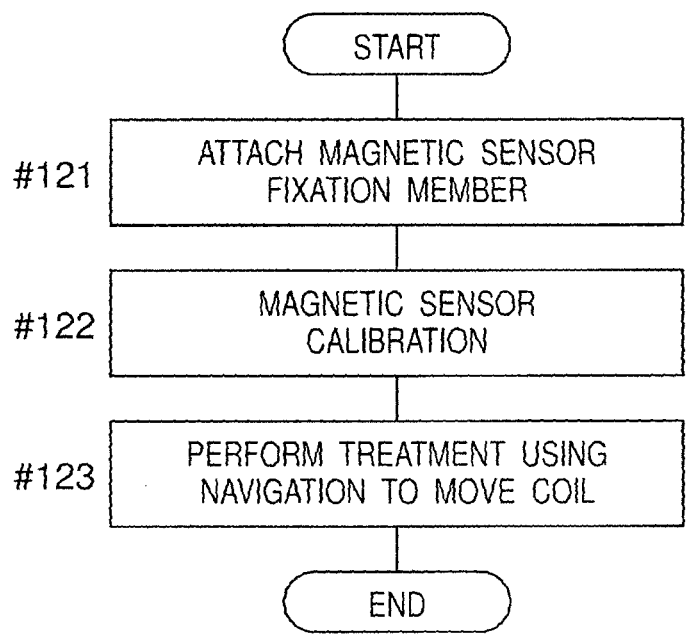
FIG. 37 is a flowchart explaining the operation method of the magnetic stimulator in a home treatment according to the second embodiment.

An operation method of the magnetic stimulator provided with the data set analyzing unit 120 thus configured is described with reference to flowcharts of FIG. 36 and FIG. 37.

First, in the hospital (see FIG. 36), in step #101, the patient wears the magnetic field sensor fixation member 50. At this time, calibration for an attachment position at which the magnetic field sensor fixation member 50 is attached is performed (step #102). Then, the doctor determines the optimum stimulating position according to the conventional method using the optical tracking system (step #103). Subsequently, in step #104, the data sets for the optimum stimulating position and the plurality of (large number of) positions around this position are collected and recorded in the recording section 123 of the data set analyzing unit 120.

Next, in the home treatment, similarly to the case of the treatment in the hospital, first, the patient wears the magnetic field sensor fixation member 50 (step #121). At this time, the patient wears the magnetic field sensor fixation member 50 in the same manner as in the hospital. However, it is difficult in practice to wear the magnetic field sensor fixation member 50 always without any displacement of the position, it is necessary to perform calibration for the attachment position at which the magnetic field sensor fixation member 50 is attached (step #122). Then, the user manipulates to move the coil holder 12 while watching the display screen utilizing a navigating function of the user interface section 128 of the data set analyzing unit 120, and guides the stimulation coil 11 to the position and posture that are as close as possible to the optimum stimulating position and posture to perform the treatment (step #123). It should be noted that at this time, the coil holder 12 can be manipulated to be moved while the base plate 42 (and the Polaris markers 43) that are fixed to the coil holder 12 with such as a screw member is removed. Further, the base plate 52 and the Polaris markers 53 that are attached to the magnetic field sensor fixation member 50 are also unnecessary.

The calibration for the attachment position of the magnetic field sensor fixation member 50 performed in step #102 and in step #122 can be performed, for example, in the following manner. It should be noted that in this case, it is preferable that, in order to attach the magnetic field sensor fixation member 50 to a position within a desired range, a certain attachment position be determined to be a reference attachment position within the desired range, a magnetic marker, for example, be applied according to the position of the nose or the ear in a state in which the patient is wearing the magnetic field sensor fixation member 50 at the reference attachment position, magnetic field data of the magnetic marker be obtained by the sensor system, and the magnetic field data be recorded as reference magnetic field data for calibration.

Then, in the same manner as the case when the reference magnetic field data has been obtained for each of the cases in the hospital and the home treatment, the magnetic marker is applied according to the position of the nose or the ear, the magnetic field data of the magnetic marker is obtained by the sensor system, and the attachment position of the magnetic field sensor fixation member 50 in each case can be adjusted such that the obtained magnetic field data matches the reference magnetic field data as much as possible.

It should be noted that instead of additionally setting the reference magnetic field data for calibration, the calibration can be performed by recording the magnetic field data of the magnetic marker obtained in the hospital, and by adjusting the attachment position of the magnetic field sensor fixation member 50 in the home treatment such that the magnetic field data of the magnetic marker obtained in the home treatment matches the magnetic field data obtained in the hospital as much as possible.

For the method using the data sets as described above, an experiment for examining time required and a movement locus for guiding to final guiding position and posture corresponding to the optimum stimulating position and posture, errors of the final guiding position and posture from the optimum stimulating position and posture, and an influence of the number of the data sets was conducted.

The errors of the final guiding position and posture from the optimum stimulating position and posture were measured using POLARIS. As the errors, the center position error, the roll angle error, the pitch angle error, and the yaw angle error of the stimulation coil were measured.

In this experiment, the head Hm of a dummy was used in place of the patient s head, and an operator of the coil holder 12 was a subject. There were a plurality of subjects (three, for example), and all of the subjects were non-medical staff, and took training for a guiding operation for a predetermined time period (a few minutes, for example) so as to become familiar with Open GL prior to the experiment. It should also be noted that specification of the optimum stimulating position and posture and collection of data sets in this experiment are also performed by non-medical staff (one of the inventors). It should be noted that in the system used in this experiment, a sampling rate of the data is 4 Hz, for example.

Further, the experiment was performed for two patterns in which the number of the data sets was 500 and 1000. These data sets were collected focusing a region near the optimum stimulating position. Each subject performed the guiding operation for three times for each pattern, six times in total.

As a result of the above experiment, facts listed blow were confirmed.

a) Regardless of the subject, the errors were significantly reduced in the pattern in which the number of the data sets is 1000, as compared to the pattern of 500 data sets.

According to this method, even if the magnetic fields generated by the permanent magnets do not completely match the magnetic field of the data set, the data set having the closest magnetic field is extracted and its position data is displayed. Specifically, even if it is recognized that the guiding operation has ended on the system, an error can occur from the data set specified as the optimum stimulating position. Therefore, it is considered that when the number of the data sets is small, the errors between the actual position of the stimulation coil and the position of the stimulation coil displayed on the Open GL increase on average.

b) Further, in the pattern in which the number of the data sets was 1000, the errors were mostly within requested specification errors listed below. By further increasing the number of the data sets, it is conceivable that the requested specification errors can be satisfied in all cases.

It should be noted that, the requested specifications are calculated preferably based on a clinical research. In this embodiment, similarly to the first embodiment, it is set that the errors of the center position and posture of the coil are within ranges listed below, for example.

The error of the center position of the coil: within 5 [mm]

The error of the posture of the coil: within 5 [deg] with respect to each axis of the coil c) When the number of the data sets was 1000, the time period required for guiding is generally longer than in the pattern of 500 data sets.

According to this experiment, a condition for ending the guiding operation is when the same data set as that specified for the optimum stimulating position and posture is displayed on Open GL. Therefore, even if the errors are within the requested specification errors, the guiding operation does not end unless the data set matches. It takes time for guiding when the number of the data sets is large, as the data set is more probably recognized not to be the data set of the optimum stimulating position and posture.

However, in this experiment, it takes only 55 seconds at maximum, and this method can be said to be sufficiently practical. Further, the time period required for guiding is expected to be reduced as the subject (or the patient) becomes more familiar with the operation. Moreover, it is possible to further reduce the time period by setting the condition to end the guiding operation when the errors are within the requested specification errors, for example.

As described above, the position of the stimulation coil 11 is calculated and displayed in the user interface section (display screen) 128 based on the comparison between the data relating to the intensity and direction of the magnetic field detected by the magnetic field sensors either before or during the magnetic stimulation by the stimulation coil 11 and the information (data set) recorded in the recording section 123. This contributes to downsizing, cost reduction, and facilitation of handling of the magnetic stimulator without requiring a complicated algorithm, and in turn, allows the patient M to perform the transcranial magnetic stimulation treatment at home or at the personal doctor s office in the neighborhood continuously and repeatedly on a daily basis.

Further, although the effectiveness of the method using the data sets was examined as described above, this method additionally involves the step collecting the data sets, as compared to the method using the inverse analysis of the magnetic field. For example, in the case of the experiment, as the sampling rate of the data is 4 Hz, for example, it takes about 5 minutes in order to collect 1000 data sets.

When actually applying the method using the data sets in medical practice, it is necessary for the doctor to determine the optimum stimulating position on the patient s head, and then to collect the data sets for a large number of points around this position. This collecting operation of the data sets is a burden for the doctor. Therefore, it is desirable that a method of relieving the burden of the collecting operation of the data sets is introduced as well, such as reducing the time required for collecting the data sets.

In order to reduce the time required for collecting the data sets, it is advantageous to allow the guidance based on a fewer data sets. One example of the method allowing this is a method of interpolating the data sets with each other using an interpolation method. Examples of the interpolation method include known methods such as a method utilizing a multiple regression analysis and a method utilizing a weighted mean.

As one example of the method for interpolating the data set, the method utilizing the multiple regression analysis is described.

For example, it is possible to interpolate using [number of sensors×3 (axis)−2] (10, where the number of the sensors is 4) of n data sets. In this case, a larger number of sensors increase trustability of the interpolation.

The magnetic field data obtained by the magnetic field sensors in real time (that is, the magnetic field data at the position at which the patient places the coil) is taken as A. A is compared with the magnetic field data $B_1$ (i=1, 2, . . . , N) of the N data sets, and the f value expressed by Formula 22 for each data set is obtained ($f_1$-$f_N$).

$$f_i = \tfrac{1}{2}(A-B_i)^2 \quad \text{[Formula 22]}$$

Here, A is a column vector of 12 lines and 1 column in which values of three directions of x, y, and z each for the four magnetic field sensors a, b, c, and d are arranged sequentially in column, and $B_1$ is a column vector of 12 lines and 1 column in which four three-dimensional vectors $B_{ai}$, $B_{bi}$, and $B_{ci}$, and $B_{di}$ corresponding to the data set number i in Table 6 are arranged in column.

Next, 10 data sets whose f value is small are extracted out of the data sets. A composition matrix of 12 lines and 10 columns in which the 10 data sets of the magnetic field data is taken as D. When a regression coefficient vector for 10 lines and 1 column is θ, and an error vector for 12 lines and 1 column is ε, the magnetic field data A is expressed by Formula 23.

$$A = 1\theta_0 + D\theta + \varepsilon \quad \text{[Formula 23]}$$

A least-squares estimator Θ is obtained based on Formula 23. Using Θ, a position $P_A$ and a posture $R_A$ of the coil when the value detected by the magnetic field sensors is A are interpolated based on Formula 24 and Formula 25 listed below.

$$P_A = \frac{\sum_{i=1}^{10} |\Theta_i| P_i}{\sum_{j=1}^{10} |\Theta_j|} \quad \text{[Formula 24]}$$

$$R_A = \frac{\sum_{i=1}^{10} |\Theta_i| R_i}{\sum_{j=1}^{10} |\Theta_j|} \quad \text{[Formula 25]}$$

Here, $P_i$ in Formula 24 and $R_i$ in Formula 25 are the data of the coil position and posture corresponding to the 10 sets of magnetic field data extracted from the data sets.

Using the same method and based on the same conditions as in the experiment described above, an experiment of comparing time periods required for guiding the coil to the optimum stimulating position and posture and errors after the guidance for a case in which the actual number of the data sets is 500 and the interpolation method is employed and a case in which the actual number of the data sets is 1000 was performed, and substantially the same results were obtained in the both cases, and it was confirmed that the interpolation method is effective.

Further, by contriving ways to collect the data sets centering the optimum stimulating position, it is considered to allow the guidance with a fewer number of the data sets.

In a case in which the coil is guided to the optimum stimulating position and posture using the data sets, in order to match the position and posture of the coil with optimum stimulating position and posture as much as possible, it is desired that there be many data sets in a region near the optimum stimulating position. By contrast, collection of a large number of the data sets is not required for a region that is largely distant from the optimum stimulating position, as compared to the region near the optimum stimulating position.

Depending on a disease treated by the transcranial magnetic stimulation treatment, which portion of the brain is to be stimulated is known in some cases. For example, in a case of a neuropathic pain, it is considered to be desirable to stimulate the primary motor cortex (see paragraphs [0026], and others in Patent Literature 1, for example). Further, the optimum stimulating portion is localized in general (in a case of a neuropathic pain, not greater than a diameter of 20 mm, and advantageously not greater than a diameter of 10 mm for example, see paragraph [0028] in Patent Literature 1).

Therefore, in terms of the collection of the data sets, it is effective that the data collection is performed in the high density focusing the region near the optimum stimulating portion, while the data collection is performed in the relatively lower density in the region largely distant form the optimum stimulating portion. That is, it is possible to reduce the number of the collected data sets while maintaining the time period and accuracy required for guiding the coil to the optimum stimulating position and posture.

It should be noted that, the optimum stimulating portion is different depending on the neural disease as a treatment target. In this case, it is possible to provide the same effect as in the case of the neuropathic pain by performing the data collection in the high density focusing a specified region corresponding to the neural disease, while performing the data collection in the relatively lower density in the region largely distant form the specified region.

Further, while not reducing the number of the data sets, as one method for improving effectiveness in collecting the data sets, it is possible to facilitate the determination of the position by partitioning the patient s head in a mesh and displaying coordinates.

Although the effectiveness of the collection of the data sets can be improved by employing the method as described above, this still places a burden for the doctor as long as the collection of the data sets is performed by the doctor.

Therefore, it is possible to relieve the burden for the doctor by dividing the collecting operation of the data sets into an operation that is required to be performed by the doctor and an operation that can be performed by someone other than the doctor.

Describing more specifically, while the optimum stimulating position is required to be determined by the doctor, the collecting operation of the data sets itself can be performed by someone other than the doctor. In other words, the determination of the optimum stimulating position is required to be performed by the doctor, using the three-dimensional position measuring device (optical tracking system, for example) in the hospital to the patient as the treatment target. By contrast, the collecting operation of the data sets other than the determination of the optimum stimulating position and posture can be performed by someone other than the doctor at a place other than the hospital, without the three-dimensional position measuring device installed in the hospital, or even without the patient.

Therefore, the collection of the data sets can be performed separately from the determination of the optimum stimulating position and posture by the doctor in the hospital. For example, it is suitable to perform the collecting operation as a part of a pre-shipment examination by a manufacturer (maker) of the magnetic stimulator.

Specifically, the data sets are obtained in a coordinate system A using a three-dimensional position measuring device of the maker on the maker s side. By contrast, the optimum stimulating position and posture is obtained in a different coordinate system B in the hospital using the three-dimensional position measuring device in the hospital. Registration of a relation between the coordinate system A and the coordinate system B is easily carried out using a known method as will be described later. Then, by converting the optimum stimulating position and posture obtained in the coordinate system B into the coordinate system A, it becomes possible to perform navigation using the data sets obtained on the maker s side. As a result, the burden for the doctor involved in the collection of the data sets is significantly relieved.

In this case, it is preferable that the recording section of the data set analyzing unit serve to record information of at least the position (preferably, of the position and posture) of the magnetic field generating means as the information of positions (and postures) in a plurality of different coordinate systems, and be provided with a coordinate converting function that allows matching between the information of the positions (and postures) in the plurality of different coordinate systems with each other to allow comparison.

A specific example of the registration between the coordinate system A by the three-dimensional position measuring device by the maker and the coordinate system B by the three-dimensional position measuring device in the hospital is now described. It is possible to employ the method using Formula 1 and Formula 2 in this case as well, Specifically, as described below.

(1) First, four feature points that can be measured stably and are not in the same plane are determined on the magnetic field sensor fixation member 50.

(2) Next, position coordinates of the four feature points in the coordinate system A including: $(x_1, y_1, z_1)$, $(x_2, y_2, z_2)$, $(x_3, y_3, z_3)$, and $(x_4, y_4, z_4)$ are obtained using the three-dimensional position measuring device of the maker.

(3) Further, position coordinates of the four feature points in the coordinate system B including: $(x_1, y_1, z_1)$, $(x_2, Y_2, Z_2)$, $(X_3, Y_3, Z_3)$, and $(X_4, Y_4, Z_4)$ are obtained using a three-dimensional position measuring device in the hospital.

(4) The coordinate conversion matrix T is calculated based on Formula 1.

(5) As expressed by Formula 2, by applying the coordinate conversion matrix T, the position coordinate (X, Y, Z) of an arbitrary feature point (thus, of the optimum stimulating position) obtained in the coordinate system B (the three-dimensional position measuring device in the hospital) can be converted into the position coordinate (x, y, z) in the coordinate system A by the three-dimensional position measuring device of the maker, and whereby the navigation using the data sets is possible.

It should be noted that when the data sets (including values calculated by interpolation) at a sufficiently high density are prepared by the maker, it is possible to eliminate the necessity of the coordinate conversion process (that is, registration) itself. That is, the doctor determines the optimum stimulating position and posture in the hospital, and the three-dimensional position and posture corresponding to the magnetic fields at this time (not the observed values in the hospital, but the values called from the data sets or calculated by interpolation) can be taken as the optimum stimulating position and posture as they are by referring to the data sets prepared by the maker. In this case, specifically, it may be said that the above described coordinate conversion process is performed using the data sets.

The above process is described more specifically. <In the maker s site>: in the pre-shipment examination, for example a) The magnetic field sensor fixation member (a pair of eyeglasses provided with the magnetic field sensors, for example) is set on a head model based on a normal configuration of an adult s head.

b) Using the three-dimensional position measuring device (coordinate system A) installed in the maker s site, combinations (data sets) of the magnetic fields generated by the permanent magnets attached to the coil holder along with the stimulation coil (measured by the magnetic field sensors attached to the pair of eyeglasses) and the three-dimensional position and posture of the stimulation coil in the coordinate system A are collected while operating to move the coil holder. At this time, considering such as a difference between the head model and the actual patient s head and the displacement of the pair of eyeglasses from the attachment position, the data sets are collected as many as possible.

<In the Hospital>: In the Initial Treatment a) The patient wears the magnetic field sensor fixation member (a pair of eyeglasses provided with the magnetic field sensors, for example).

b) Using the three-dimensional position measuring device (coordinate system. B) installed in the hospital, combinations of the magnetic fields generated by the permanent magnets attached to the coil holder along with the stimulation coil (measured by the magnetic field sensors attached to the pair of eyeglasses), the three-dimensional position and posture of the stimulation coil in the coordinate system A (estimated from the data sets obtained by the maker), and the three-dimensional position and posture of the stimulation coil in the coordinate system. B are collected for a few points (at least four points) while operating to move the coil holder.

c) Based on correspondence between the coordinate system A and the coordinate system B for these points, a coordinate conversion matrix between the coordinate system A and the coordinate system B is obtained employing the registration described above.

d) Next, the doctor determines the optimum stimulating position and posture in the coordinate system B.

e) Using the coordinate conversion matrix obtained in (c), the optimum stimulating position and posture are converted into the coordinate system A and recorded.

<At Home>

In addition to the data sets (coordinate system A) collected by the maker, the data set for the optimum stimulating position and posture obtained in the hospital converted into the same coordinate (coordinate system A) is additionally recorded, and the patient can perform the navigation operation as usual.

As described above, it is possible to minimize the burden for the doctor without making any substantial change to the outline of the method using the data sets.

Here, it is described how to apply the method of contriving ways to collect the data sets centering the optimum stimulating position described above to the collection of the data sets on the maker s side.

For example, as described above, there is a case in which which portion of the brain is to be stimulated in known depending on a disease treated by the transcranial magnetic stimulation treatment. Therefore, when collecting the data sets on the maker s side, by roughly recognizing a region on the head model where the optimum stimulating portion is possibly positioned and performing the data collection in the high density focusing this region, while performing the data collection in the relatively lower density in the region largely distant form the specified region, it is possible to efficiently perform the collection of the data sets.

Further, it is also conceivable that after information relating to the patient s head and the optimum stimulating position are obtained in the hospital, the information is provided for the maker, and the maker collects the data sets suitable for the patient based on the provided information. In this case, the maker can collect the data in the high density focusing the region near the optimum stimulating position based on the position information for the optimum stimulating position, while collecting the data in the relatively lower density in the region largely distant form the optimum stimulating position. In this case, by providing the position information of the optimum stimulating position from the hospital (even if it is rough), it is possible to efficiently perform the collection of the data sets.

In the above description, the data sets including the data set for the optimum stimulating position and posture are obtained mostly using the three-dimensional position measuring device such as an optical tracking device. However, instead of this, it is possible to obtain the data sets using the inverse analysis of the magnetic fields described in the first embodiment.

Further, by employing the method using the inverse analysis of the magnetic fields and the method using the data sets in combination, it is possible to configure to guide the stimulation coil to the optimum stimulating position and posture more efficiently.

In this case, for example, based on a configuration in which the stimulation coil is guided according to the method using the inverse analysis of the magnetic fields in a region where the data set is not obtained (that is, a region somewhat distant from the optimum stimulating position), and the stimulation coil is guided according to the method using the data sets in a region where the data sets are obtained (that is, a region relatively close to the optimum stimulating position), it is possible to efficiently and smoothly guide the stimulation coil even when the number of the data sets is relatively small.

As described above, when the coil is guided to the optimum stimulating position and posture using the data sets, it is desirable that the number of the data sets be large in order to cause the position and posture of the coil to match the optimum stimulating position and posture as much as possible, and in particular, the number of the data sets near the optimum stimulating position largely influences the accuracy for the guiding position and posture of the coil. Therefore, it is conceivable to employ the inverse analysis method in a last process for guiding the coil, instead of guiding the coil to the end only based on the data sets. In this case, it is possible to reduce the number of the data sets in the region near the optimum stimulating position to some extent.

Further, it is also conceivable that the method using the inverse analysis is employed in the region where the coil position is distant from the optimum stimulating position more than a certain degree and where data sets are not obtained, such as in the beginning of the coil guiding process, and the method using the data sets is employed and a rough positioning is performed in the region where the data sets are obtained as the coil guiding process advances, and finally the method using the inverse analysis is employed in the last process for guiding the coil to perform final positioning.

According to the above embodiments, basically, the stimulation coil is manipulated to be relatively displaced with respect to the fixed patient s head. However, instead of this, it is possible that the stimulation coil is fixed and the patient s head moves to be relatively displaced with respect to the fixed stimulation coil. Alternatively, the present invention can be effectively applied to a case in which the patient s head and the stimulation coil both move to be relatively displaced.

One example of such an embodiment, in particular, a positioning method to the optimum stimulating position in the treatment at home is exemplified in the following.

First, similarly to the previous embodiments, the magnetic field sensors as the magnetic field detecting means are fixed to the patient s head using the fixing means such as a pair of eyeglasses. On the other hand, the stimulation coil is fixed using the holder fixation member so as to correspond to a rough stimulating position (a region corresponding to the primary motor cortex, for example) on the head.

After the setting is completed, the positioning can be basically performed according to a process corresponding to the process of the flowchart shown in FIG. 5. Describing with reference to the flowchart in FIG. 5, in this embodiment, in step #22, the patient moves his head so as to match the optimum position. In step #23, similarly to the previous embodiments, the deviation (misalignment) of the stimulation coil from the optimum position and posture is detected. Then, in step #24, the user interface section instructs the patient how the patient should move his own head. Specifically, the movement of the patient s head is navigated such that the stimulation coil is positioned at the optimum position and posture. Through this process, similarly to the previous embodiments, it is possible to perform the treatment at the optimum stimulating position.

It should be noted that, in step #22, it is possible for the patient to manipulate to displace the stimulation coil while moving his own head. In this case, by the user interface section functioning as the instructing means for guiding to manipulate to displace the stimulation coil and as the instructing means for guiding to move the patient s head, it is possible to effectively navigate the stimulation coil to the optimum stimulating position and posture.

All of the above embodiments describe the case of the use in the transcranial magnetic stimulation treatment for relieving a neuropathic pain by applying magnetic stimulation to the brain nerve by the stimulation coil provided on the surface of patient s scalp. However, the present invention is not limited to such an example, and can be effectively utilized in other applications of the magnetic stimulation.

As described above, it should be appreciated that the present invention is not limited to the embodiments described above, and various modifications and improvements in design can be made without departing from the spirit of the invention.

INDUSTRIAL APPLICABILITY

The present invention relates to the magnetic stimulator for applying magnetic stimulation to a particular portion of the subject, and can be effectively utilized, for example, as a device used in the transcranial magnetic stimulation treatment, in which the magnetic stimulation is applied to the brain nerve, for example, by the stimulation coil provided on the surface of the patient s scalp.

EXPLANATION OF REFERENCE SYMBOLS

10 Transcranial magnetic stimulator
11 Stimulation coil
12 Coil holder 13 Magnetic field sensor
14 Pair of eyeglasses
15 Cable
16 Magnetic stimulation control device
20 Magnetic field analyzing unit
22, 122 Signal analyzing section
23 Storage section
24, 124 Comparing section
25, 125 User information output section
28, 128 User interface section
41 Permanent magnet
50 Magnetic field sensor fixation member
51 Magnetic field sensor
120 Data set analyzing unit
123 Recording section
M Patient

The invention claimed is:

1. A magnetic stimulator for applying magnetic stimulation to a particular portion of a subject, comprising:
   (a) a magnetic field generator including at least a stimulation coil which generates a magnetic field so as to apply the magnetic stimulation, the magnetic field comprising a dynamic magnetic field;
   (b) an operating device which is configured to operate to displace a relative position of the magnetic field generator with respect to the particular portion of the subject;
   (c) a plurality of magnetic field sensors each of which senses a magnetic field intensity of each of predetermined directional components in the magnetic field generated by the magnetic field generator;
   (d) a magnetic field analyzing device implemented by a hardware processor and a memory, wherein:
   (d1) the memory stores three-dimensional reference data of the stimulation coil, the three-dimensional reference data corresponding to an optimum position and posture to perform a transcranial magnetic stimulation treatment to the subject by means of the stimulation coil,
   (d2) the hardware processor calculates a current position and posture of the stimulation coil by
      recording data obtained by each of the plurality of magnetic field sensors as a plurality of degrees of freedom relating to three-dimensional position and posture of the stimulation coil are changed at respective positions in a three dimensional space and storing sensed data in a form of a table;
      by means of the plurality of magnetic field sensors, sensing a current magnetic field generated by the magnetic field generator including the stimulation coil; and
      comparing the sensed data relating to the current magnetic field and the recorded data to determine the current position and posture of the stimulation coil, and
   (d3) the hardware processor compares three-dimensional data of the current position and posture of the stimulation coil with the three-dimensional reference data to obtain a deviation of the three-dimensional data of the current position and posture from the three-dimensional reference data; and
   (e) a user interface which generates and indicates instruction information indicating an operation of displacement of the relative position of the magnetic field generator with respect to the particular portion of the subject to be performed by the operating device based upon the deviation obtained by the hardware processor.

2. The magnetic stimulator according to claim 1, further comprising:
   a fixing device configured to fix each of the plurality of magnetic field sensors to a predetermined relative position with respect to the particular portion of the subject.

3. The magnetic stimulator according to claim 2, wherein the fixing device is selected from a pair of eyeglasses, a pair of earpieces, a pair of headphones, and a headband.

4. The magnetic stimulator according to claim 1, wherein the magnetic field generator is attached to the operating device.

5. The magnetic stimulator according to claim 1, wherein the hardware processor calculates a position of the magnetic field generator as a position of a magnetic field source obtained based on an inverse analysis method using information relating to an intensity and a direction of the magnetic field sensed by each of the plurality of magnetic field sensors.

6. The magnetic stimulator according to claim 1, wherein the hardware processor further performs:
   storing information relating to a position of the magnetic field generator and a piece of information relating to an intensity and a direction of the magnetic field sensed by each of the plurality of magnetic field sensors previously recorded in pairs for at least a plurality of positions of the magnetic field generator, and
   calculating the position of the magnetic field generator based on comparison between a given piece of information relating to the intensity and the direction of the magnetic field and the piece of information previously recorded, the given piece of information being based on the intensity and the direction of the magnetic field sensed by each of the plurality of magnetic field sensors either before or during the magnetic stimulation.

7. The magnetic stimulator according to claim 6, wherein the hardware processor is capable of recording information of the position of the magnetic field generator as pieces of position information in a plurality of different coordinate systems, and includes capable of performing the comparison by matching the pieces of position information in the plurality of different coordinate systems with each other.

8. The magnetic stimulator according to claim 1, the hardware processor further performs:
   storing a plurality of pieces of information relating to an intensity and a direction of the magnetic field previously recorded, the magnetic field being sensed by each of the plurality of magnetic field sensors in a state in which the magnetic field generator is positioned either at a position at which the magnetic stimulation is to be applied to the particular portion of the subject or within an allowable range near this position, wherein
   the user interface generates and provides the instruction information based on a result of comparison between a given piece of information relating to the intensity and the direction of the magnetic field and the plurality of pieces of information previously recorded, the given piece of information being based on the intensity and the direction of the magnetic field that is sensed by each of the plurality of magnetic field sensors either before or during the magnetic stimulation.

9. The magnetic stimulator according to claim 1, wherein the magnetic field generator generates the dynamic magnetic field and a static magnetic field.

10. The magnetic stimulator according to claim 9, wherein
the plurality of magnetic field sensors sense the dynamic magnetic field and the static magnetic field generated by the magnetic field generator.

11. The magnetic stimulator according to claim 10, wherein
the plurality of magnetic field sensors sense the static magnetic field generated by the magnetic field generator in a state in which generation of the dynamic magnetic field by the magnetic field generator is prevented.

12. The magnetic stimulator according to claim 10, wherein
the plurality of magnetic field sensors sense only the dynamic magnetic field generated by the magnetic field generator.

13. The magnetic stimulator according to claim 1, wherein
the magnetic field generator generates only the dynamic magnetic field.

14. The magnetic stimulator according to claim 13, wherein
the plurality of magnetic field sensors sense only the dynamic magnetic field generated by the magnetic field generator.

15. The magnetic stimulator according to claim 1, wherein
the hardware processor provides at least one of visual information and auditory information.

16. The magnetic stimulator according to claim 15, wherein
the user interface provides the instruction information as the auditory information, and configured to change at least one of a volume level, a musical scale, and a tone according to either an amount of the displacement of the relative position of the magnetic field generator with respect to the particular portion of the subject to be performed by the operating device or an amount of body movement to be made by the subject.

17. The magnetic stimulator according to claim 15, wherein
the user interface provides the instruction information as the visual information, and is configured to change a color of instruction according to either an amount of the displacement of the relative position of the magnetic field generator with respect to the particular portion of the subject to be performed by the operating device or an amount of body movement to be made by the subject.

18. The magnetic stimulator according to claim 1, wherein
the magnetic stimulator is configured to apply the magnetic stimulation to at least a particular portion of a brain of the subject for the transcranial magnetic stimulation treatment.

19. A magnetic stimulator for applying magnetic stimulation to a particular portion of a subject, comprising:
(a) a magnetic field generator including at least a stimulation coil which generates a magnetic field so as to apply the magnetic stimulation, the magnetic field comprising a dynamic magnetic field;
(b) a holding device which is configured to hold the magnetic field generator near the particular portion of the subject;
(c) a plurality of magnetic field sensors each of which senses a magnetic field intensity of each of predetermined directional components in the magnetic field generated by the magnetic field generator; and
(d) a magnetic field analyzing device implemented by a hardware processor and a memory, wherein:
(d1) the memory stores three-dimensional reference data of the stimulation coil, the three-dimensional reference data corresponding to an optimum position and posture to perform a transcranial magnetic stimulation treatment to the subject by means of the stimulation coil,
(d2) the hardware processor calculates a current position and posture of the stimulation coil by
recording data obtained by each of the plurality of magnetic field sensors as a plurality of degrees of freedom relating to three-dimensional position and posture of the stimulation coil are changed at respective positions in a three dimensional space and storing the sensed data in a form of a table;
by means of the plurality of magnetic field sensors, sensing a current magnetic field generated by the magnetic field generator including the stimulation coil; and
comparing the sensed data relating to the current magnetic field and the recorded data to determine the current position and posture of the stimulation coil,
(d3) the hardware processor compares three-dimensional data of the current position and posture of the stimulation coil with the three-dimensional reference data to obtain a deviation of the three-dimensional data of the current position and posture from the three dimensional three-dimensional reference data, and
(e) a user interface which generates and indicate instruction information indicating a body movement that the subject is to take in order to apply the magnetic stimulation to the particular portion, the sensing being made by the plurality of magnetic field sensors either before or during the magnetic stimulation.

20. The magnetic stimulator according to claim 19, further comprising:
a fixing device configured to fix the plurality of magnetic field sensors to a predetermined relative position with respect to the particular portion of the subject.

21. The magnetic stimulator according to claim 20, wherein
the fixing device is selected from a pair of eyeglasses, a pair of earpieces, a pair of headphones, and a headband.

22. The magnetic stimulator according to claim 19, wherein
the user interface generates and provides the instruction information by calculating a position of the magnetic field generator as a position of a magnetic field source obtained based on an inverse analysis method using information relating to an intensity and a direction of the magnetic field sensed by each of the plurality of magnetic field sensors.

23. The magnetic stimulator according to claim 19, wherein the hardware processor further performs:
storing information relating to a position of the magnetic field generator and a piece of information relating to an intensity and a direction of the magnetic field sensed by each of the plurality of magnetic field sensor previously recorded in pairs for at least a plurality of positions, wherein
the user interface generates and provides the instruction information by calculating the position of the magnetic field generator based on comparison between a given piece of information relating to the intensity and the direction of the magnetic field and the piece of information previously recorded, the given piece of information being based on the intensity and the direction of the magnetic field sensed by each of the plurality of magnetic field sensors either before or during the magnetic stimulation.

24. The magnetic stimulator according to claim 23, wherein
the hardware processor is capable of recording information of the position of the magnetic field generator as pieces of position information in a plurality of different coordinate systems, and capable of performing the comparison by matching the pieces of position information in the plurality of different coordinate systems with each other.

25. The magnetic stimulator according to claim 19, wherein the hardware processor further performs:
storing a plurality of pieces of information relating to an intensity and a direction of the magnetic field previously recorded, the magnetic field being sensed by each of the plurality of magnetic field sensors in a state in which each of the plurality of magnetic field sensors is positioned either at a position at which the magnetic stimulation is to be applied to the particular portion of the subject or within an allowable range near this position, and
the user interface generates and provides the instruction information based on a result of comparison between a given piece of information relating to the intensity and the direction of the magnetic field and the plurality of pieces of information previously recorded, the given piece of information being based on the intensity and the direction of the magnetic field sensed by each of the plurality of magnetic field sensors either before or during the magnetic stimulation.

26. The magnetic stimulator according to claim 19, wherein
the magnetic field generator generates the dynamic magnetic field and a static magnetic field.

27. The magnetic stimulator according to claim 26, wherein
the plurality of magnetic field sensors sense the dynamic magnetic field and the static magnetic field generated by the magnetic field generator.

28. The magnetic stimulator according to claim 27, wherein
the plurality of magnetic field sensors sense the static magnetic field generated by the magnetic field generator in a state in which generation of the dynamic magnetic field by the magnetic field generator is prevented.

29. The magnetic stimulator according to claim 26, wherein
the plurality of magnetic field sensors sense only the dynamic magnetic field generated by the magnetic field generator.

30. The magnetic stimulator according to claim 19, wherein
the magnetic field generator generates only the dynamic magnetic field.

31. The magnetic stimulator according to claim 30, wherein
the plurality of magnetic field sensors sense only the dynamic magnetic field generated by the magnetic field generator.

32. The magnetic stimulator according to claim 19, wherein
the user interface provides at least one of visual information and auditory information.

33. The magnetic stimulator according to claim 32, wherein
the user interface provides the instruction information as the auditory information, and configured to change at least one of a volume level, a musical scale, and a tone according to either an amount of displacement of the relative position of the magnetic field generator with respect to the particular portion of the subject by the holding device or an amount of body movement to be made by the subject.

34. The magnetic stimulator according to claim 32, wherein
the user interface provides the instruction information as the visual information, and configured to change a color of instruction according to either an amount of displacement of the relative position of the magnetic field generator with respect to the particular portion of the subject by the holding device or an amount of body movement to be made by the subject.

35. The magnetic stimulator according to claim 19, wherein
the magnetic stimulator is configured to apply the magnetic stimulation to at least a particular portion of a brain of the subject for the transcranial magnetic stimulation treatment.

\* \* \* \* \*